United States Patent [19]

Ehrenberg et al.

[11] Patent Number: 5,502,174
[45] Date of Patent: Mar. 26, 1996

[54] REACTIVE DYESTUFFS BASED ON A SUBSTITUTED BARBITURIC ACID

[75] Inventors: Stefan Ehrenberg, Cologne; Aloysius Engel, Leverkusen; Hermann Henk, Cologne, all of Germany

[73] Assignee: Bayer Aktiengesellschaft, Leverkusen, Germany

[21] Appl. No.: 296,308

[22] Filed: Aug. 25, 1994

[30] Foreign Application Priority Data

Sep. 1, 1993 [DE] Germany ................. 43 29 421.9

[51] Int. Cl.$^6$ ............ C09B 62/006; C09B 62/08; C09B 62/507; D06P 1/38
[52] U.S. Cl. ............ 534/635; 534/642; 534/775; 534/781; 534/784; 8/549
[58] Field of Search ............ 534/635, 642, 534/775, 784

[56] References Cited

U.S. PATENT DOCUMENTS

| | | | |
|---|---|---|---|
| 2,910,464 | 10/1959 | Fasciati et al. | 534/635 X |
| 3,697,500 | 10/1972 | Ackermann et al. | 534/635 |
| 4,049,661 | 9/1977 | Seiler et al. | 534/635 X |
| 4,182,713 | 1/1980 | Goebel | 548/259 |
| 4,354,968 | 10/1982 | Kramer et al. | 534/635 X |
| 4,540,776 | 9/1985 | Henk et al. | 534/635 |
| 4,556,707 | 12/1985 | Henk | 534/635 X |
| 4,877,412 | 10/1989 | Pedrazzi | 534/775 X |
| 4,894,447 | 1/1990 | Adam | 534/775 |
| 5,420,256 | 5/1995 | Eizenhofer et al. | 534/635 X |

FOREIGN PATENT DOCUMENTS

| | | | |
|---|---|---|---|
| 584289 | 9/1959 | Canada | 534/635 |
| 1239038 | 4/1967 | Germany | |
| 2901547 | 7/1980 | Germany | 534/635 |
| 3119349 | 12/1982 | Germany | 534/635 |
| 3503746 | 8/1986 | Germany | 534/635 |
| 59-217767 | 10/1992 | Japan | |

OTHER PUBLICATIONS

Patent Abstracts of Japan, Apr. 17, 1985, C Field, vol. 9, No. 88, 2 pages; JP-A-59-217767, May 25, 1983, Sumitomo Kagaku Kogyo KK, T. Miyamoto, "Azo compound and dyeing or printing method using the same".

Derwent Abstract of JP 59-217767 (Oct. 21, 1992), Week 9246, p. 116; "New azo dyes cpds.—esp. useful for dyeing cellulosic materials", Sumitomo Chem. Co.

*Primary Examiner*—Johann Richter
*Assistant Examiner*—Fiona T. Powers
*Attorney, Agent, or Firm*—Sprung Horn Kramer & Woods

[57] ABSTRACT

Fibre-reactive dyestuffs based on barbituric acid, of the following formula $$\begin{array}{c} L^1 \\ \diagdown \\ N \end{array} \begin{array}{c} O \\ \diagup \\ \end{array} \qquad \begin{array}{c} (B-NR-X)_a \\ \diagup \\ -N=N-D \\ \diagdown \\ (B'-SO_2-M)_b \end{array} \qquad (1)$$

$$O = \begin{array}{c} \\ \diagdown \\ N \\ \diagup \\ L^2 \end{array} \begin{array}{c} \\ \\ O \end{array}$$

wherein the substituents have the meaning given in the description, are distinguished by improved properties.

9 Claims, No Drawings

REACTIVE DYESTUFFS BASED ON A SUBSTITUTED BARBITURIC ACID

The invention relates to new fibre-reaction azo dyestuffs based on barbituric acid, their preparation and use and new intermediate products.

Fibre-reactive azodyestuffs in which the coupling or the azo component is a heterocyclic component are already known. EP-A-13,879 (U.S. Pat. No. 4,540,776) relates to azo dyestuffs in which the coupling component can be a pyrimidone or also unsubstituted barbituric acid. Swiss Patent 489,582 (U.S. Paat. No. 3,697,500) relates to water-soluble disazo dyestuffs in which the coupling component can be N-methyl-N'-m-chloro-phenyl-barbituric acid. JP-A-5 9217-767 relates to azo dyestuffs which contain, as fibre-reactive groups, a halogenotriazine and a vinylsulphone or derivative thereof and a barbituric acid which is optionally substituted by alkyl or phenyl.

The known compounds have disadvantages, in particular in respect of solubility and build-up properties. The invention was based on the object of providing reactive dyestuffs which have improved properties, in particular in respect of solubility and build-up properties.

The present invention relates to fibre-reactive azo dyestuffs of the formula 1 and tautomers thereof

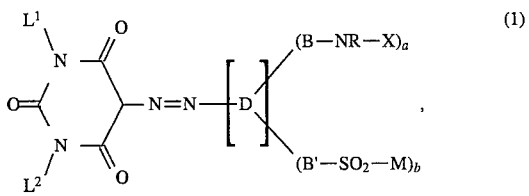

wherein a represents 0, 1 or 2, b represents 0, 1 or 2 and a+b represents 1 or 2, D=the radical of an optionally substituted aromatic or heterocyclic diazo component, which optionally contains an azo group, B and B'=independently of one another a direct bond or bridge member and in particular are linked to a ring C atom of an aromatic carbocyclic or heterocyclic ring in D, X=a fibre-reactive heterocyclic radical, R=H or optionally substituted $C_1$-$C_4$-alkyl, preferred substituents which may be mentioned being halogen, in particular Cl and F, OH, COOH, $SO_3H$ and/or $OSO_3H$, M=$CH_2$—$CH_2$—OH, CH=$CH_2$ or $CH_2$—$CH_2$—V wherein V=a radical which can be eliminated under alkaline conditions, preferably $OSO_3H$, $SSO_3H$, $OCOCH_3$, $OPO_3H_2$, $OSO_2CH_3$, SCN, $NHSO_2CH_3$, Cl, Br, F, $OCOC_6H_5$, $OSO_2$—$C_6H_5$, or $^+N(CH_3)_3$-anion (the anion is preferably Cl$^-$) and $L^1$ and $L^2$=as identical or different radicals, H or an aliphatic or aromatic group, wherein at least one of the substituents $L^1$ and $L^2$ is substituted by at least one polar radical, such as, for example, OH, COOH, $SO_3H$, $OSO_3H$ or alkoxy, or represents hydroxyl.

In addition to sulphonic acid groups, D can preferably contain alkyl groups having 1 to 4 carbon atoms, such as methyl, ethyl, propyl, isopropyl, butyl, isobutyl, secbutyl and tert-butyl, alkoxy groups having 1 to 4 carbon atoms, such as methoxy, ethoxy, propyloxy, isopropyloxy, butyloxy, isobutyloxy, sec-butyloxy and tert-butyloxy, phenoxy, acylamino groups having 1 to 6 carbon atoms, such as acetylamino, propionylamino and benzoylamino, amino groups, such as —$NH_2$—, methylamino, ethylamino and phenylamino, carboxylic acid ester groups, such as methoxycarbonyl and ethoxycarbonyl, the nitro, cyano, acetyl, carbamoyl, ureido, hydroxyl and carboxyl group and halogen, such as fluorine, chlorine and bromine.

Preferred dyestuffs of the formula 1 are those where D denotes a radical of the formula (2) or tautomers thereof

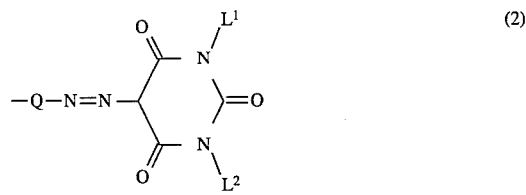

where Q=

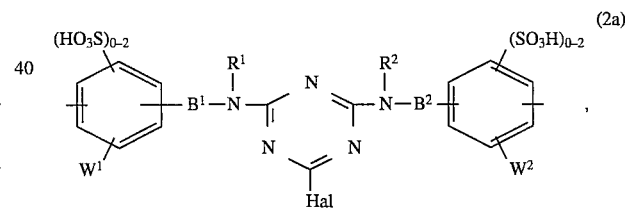

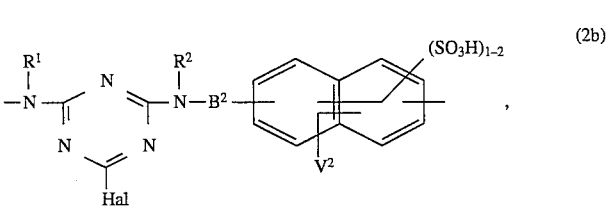

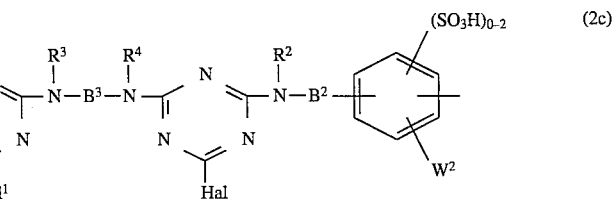

or

Q=

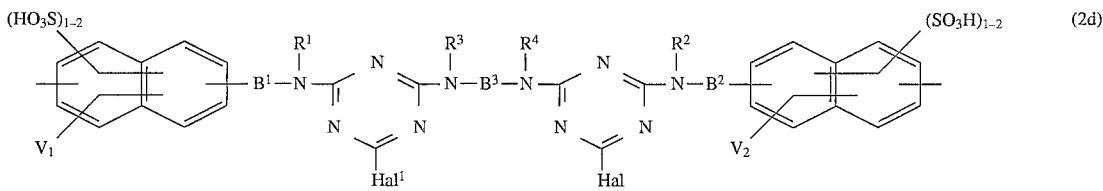

where $L^1$ and $L^2$ have the abovementioned meanings, and wherein $V^1$, $V^2$, $W^1$ and $W^2$ =independently of one another hydrogen or the substituents mentioned above for D, in particular $C_1$–$C_4$-alkyl, $C_1$–$C_4$-alkoxy, acetylamino, $NH_2$, methylamino, ethylamino, methoxycarbonyl, ethoxycarbonyl, nitro, cyano, acetyl, carbamoyl, ureido, hydroxyl, carboxyl, F, Cl or Br, Hal and $Hal^1$ =independently of one another Cl, F, pyridinium or substituted pyridinyl, $R^1$, $R^2$, $R^3$ and $R^4$ =independently of one another H or optionally substituted $C_1$–$C_4$-alkyl, preferred substituents which may be mentioned being halogen, OH, COOH, $SO_3H$ or $OSO_3H$, B and B' have the abovementioned meanings and $B^1$, $B^2$ and $B^3$ =independently of one another a direct bond or a bridge member of the following formulae

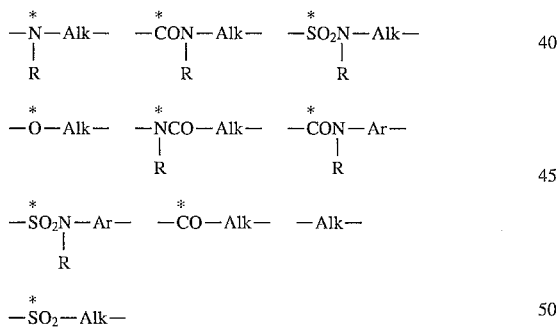

wherein the asterisk marks the linking point with a benzene or naphthalene radical, and wherein Alk denotes straight-chain or branched $C_1$–$C_6$-alkylene which is optionally interrupted by heteroatoms or groupings containing heteroatoms such as N, O or S, Ar denotes optionally substituted phenylene or naphthylene or the radical of a diphenyl or stilbene, T denotes Alk or Ar or —$\overset{*}{Alk}$—Ar— wherein Alk or Ar are optionally further substituted by F, Cl, Br, $C_1$–$C_4$-alkyl, $C_1$–$C_4$-alkoxy, carboxyl or sulpho, and E denotes F, Cl, Br, optionally substituted amino, OH, $C_1$–$C_4$-alkoxy, optionally substituted phenoxy or $C_1$–$C_4$-alkylthio.

In a particular embodiment, dyestuffs of the formula 2a to 2d wherein $W^1 = W^2$,
$V^1 = V^2$,
$R^1 = R^2$,
$Hal = Hal^1$,
$R^3 = R^4$ and
$B^1 = B^2$ are to be mentioned.

Further preferred dyestuffs of the formula (1) are those wherein a=0 and —D—($B'$—$SO_2$—M)$_b$ corresponds to a radical of the following formula (3)

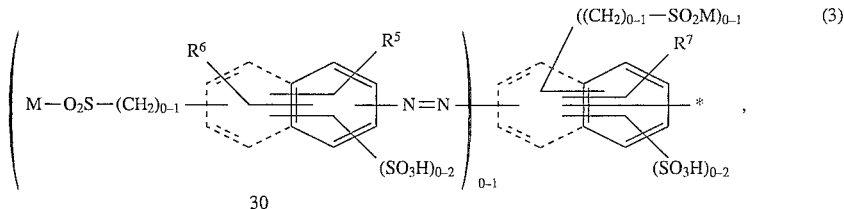

wherein $R^5$ denotes H, $C_1$–$C_4$-alkyl, Cl, Br, $C_1$–$C_4$-alkoxy or COOH, $R^6$ denotes H, $C_1$–$C_4$-alkyl, $C_1$–$C_4$-alkoxy, $SO_3H$, Cl or Br, $R^7$ denotes H, $C_1$–$C_4$-alkyl, $C_1$–$C_4$-alkoxy, Cl, Br, acylamino, in particular $C_1$–$C_4$-alkylcarbonylamino or arylcarbonylamino, such as optionally substituted phenylcarbonylamino, $C_1$–$C_4$-alkylsulphonylamino, aminocarbonylamino or arylsulphonylamino, M has the abovementioned meaning and the bond identified with * is bonded to the azo group of the formula (1).

The radical of the formula (3) is preferably derived from the following diazo components:

Aniline-4-β-sulphatoethylsulphone,
Aniline-4-β-thiosulphatoethylsulphone,
Aniline-4-vinylsulphone,
Aniline-3-β-sulphatoethylsulphone,
Aniline-3-vinylsulphone,
2-Methoxy-aniline-5-β-sulphatoethylsulphone,
2-Methoxy-aniline-5-β-thiosulphatoethylsulphone,
2-Methoxy-aniline-5-vinylsulphone,
4-Methoxy-aniline-3-β-sulphatoethylsulphone,
4-Methoxy-aniline-3-β-vinylsulphone,
2,5-Dimethoxyaniline-4-β-sulphatoethylsulphone,
2,5-Dimethoxy-aniline-4-vinylsulphone,
2Methoxy-5-methyl-aniline-4-β-sulphatoethylsulphone,
Aniline-2-β-sulphatoethylsulphone,
3-(3- or 4-aminobenzoyl)-aminophenyl-β-sulphatoethylsulphone,
2-Methoxy-5-methyl-aniline-4-vinylsulphone,
6-Carboxy-aniline-3-β-sulphatoethylsulphone,
6-Carboxyaniline-3-vinylsulphone,
2-Sulphoaniline-4-β-sulphatoethylsulphone
2-Sulphoaniline-4-vinylsulphone, 2,4-Disulphoaniline-5-vinylsulphone,
2-Naphthylamine-8-β-sulphatoethylsulphone,
2-Naphthylamine-6-β-sulphatoethylsulphone,
1-Sulpho-2-naphthylamine-6-β-sulphatoethylsulphone,
1-Naphthylamine-4-β-sulphatoethylsulphone,
1-Sulpho-2-naphthylamine-5-β-sulphatoethylsulphone,
6-Sulpho-2-naphthylamine-8-β-sulphatoethylsulphone,
2-Amino-3-sulpho-naphthalene-6,8-bis-(6² -sulphatoethylsulphone),
1-Naphthylamine-5-β-sulphatoethylsulphone,
2-Naphthylamine -5-β-sulphatoethylsulphone,
2-Naphthylamine-8-β-sulphatoethylsulphone,
8-Sulpho-2-naphthylamine-6-β-sulphatoethylsulphone,
4-Aminobenzyl-β-sulphatoethylsulphone,
3-Aminobenzyl-β-sulphatoethylsulphone,
4-Aminobenzylvinylsulphone,
3-Aminobenzylvinylsulphone,
3-Amino-4-sulphobenzyl-β-sulphatoethylsulphone,
4-Amino-3-sulphobenzylvinylsulphone,
4-Vinylsulphonyl-butanoic acid (4'-amino-3'-sulpho)-anilide
3-Amino-N-[2'-(β-sulphatoethylsulphonyl)-ethyl]-benzamide,
4-Vinylsulphonyl-butanoic acid (5'-amino-2',4'-disulpho)-anilide,
4-Amino-3-methoxy-N-(2-vinylsulphonyl-ethyl)-benzamide,
4-(β-Sulphatoethylsulphonyl)-butanoic acid (3'-amino-4'-sulpho)-anilide,
4-(β-Chloroethylsulphonyl)-butanoic acid (4'-amino-3'-sulpho)-anilide,
4-Amino-N-[2-vinylsulphonyl-ethyl]-benzamide,
3-Vinylsulphonyl-propanoic acid (4'-amino-2',5'-disulpho)-anilide,
2'-(β-Sulphatoethylsulphonyl)-3-sulpho-4-aminoazobenzene,
3'-(β-Sulphatoethylsulphonyl)-3-sulpho-4-aminoazobenzene,
4'-Methoxy-3'-(β-Sulphatoethylsulphonyl)-3-sulpho-4-aminoazobenzene,
4'-Vinylsulphonyl-2',3-disulpho-4-aminoazobenzene,
2'-(β-Sulphatoethylsulphonyl)-6-methyl-3-sulpho-4-aminoazobenzene,
3'-(β-Sulphatoethylsulphonyl)-6-methyl-3-sulpho-4-aminoazobenzene,
4'-(β-Sulphatoethylsulphonyl)-6-methyl-3-sulpho-4-aminoazobenzene,
4'-(β-Sulphatoethylsulphonyl)-2,6-dimethyl-3-sulpho-4-aminoazobenzene,
3'-(β-Sulphatoethylsulphonyl)-6-methoxy-3-sulpho-4-aminoazobenzene,
3',4'-bis-(β-Sulphatoethylsulphonyl)-6-methoxy-3-sulpho-4-aminoazobenzene,
4'-(β-Sulphatoethylsulphonyl)-6-methoxy-3-sulpho-4-aminoazobenzene,
4'-(β-Sulphatoethylsulphonyl)-2-methyl-5-methoxy-3-sulpho-4-aminoazobenzene,
4'-(β-Sulphatoethylsulphonyl)-2,5-dimethoxy-3-sulpho-4-aminoazobenzene,
3'-(β-Sulphatoethylsulphonyl)-2,5-dimethoxy-3-sulpho-4-aminoazobenzene,
2-(4'-Amino-3'-sulphophenylazo)-6-(β-sulphatoethylsulphonyl)-naphthalene,
2-(4'-Amino-6'-methyl-3'-sulphophenylazo)-1-sulpho-6-(β-sulphatoethyl-sulphonyl)-naphthalene,
2-(4'-Amino-6'-methyl-3'-sulphophenylazo)-8-sulpho-6-(β-sulphatoethylsulphonyl)-naphthalene,
2-(4'-Amino-3'-sulphophenylazo)-8-sulpho-6-(β-sulphatoethylsulphonyl)-naphthalene,
2-(4'-Amino-6'-methyl-3'-sulphophenylazo)-1,7disulpho-5-(β -sulphatoethylsulphonyl)-naphthalene, Dyestuffs which are likewise preferred are those of the formula (1) and tautomers thereof
wherein
b=0,
a=1 and the other substituents have the above meanings.

Dyestuffs which may be mentioned in particular here are those of the formula (4)

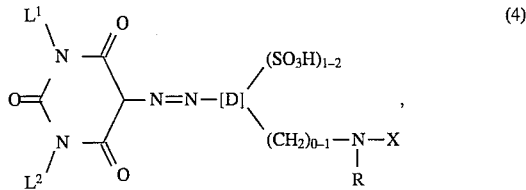

(4)

wherein

D=the radical of a benzene or naphthalene, which is optionally substituted by $C_1$–$C_4$-alkyl, $C_1$–$C_4$-alkoxy, $CO_2H$,

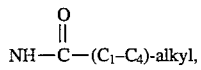

NH—CO—NH$_2$ or halogen, in particular Cl or F,
and $L^1$, $L^2$, R and X have the above meanings.

Dyestuffs which are likewise preferred are those of the formula (1) and tautomers thereof wherein b=0, a=1 and D denotes a radical, containing sulphonic acid groups, of a heterocyclic diazo component which is optionally substituted, preferably by $C_1$–$C_4$-alkyl, $C_1$–$C_4$-alkoxy,

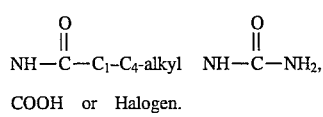

COOH or Halogen.

Particularly preferred dyestuffs here are those of the formula (5)

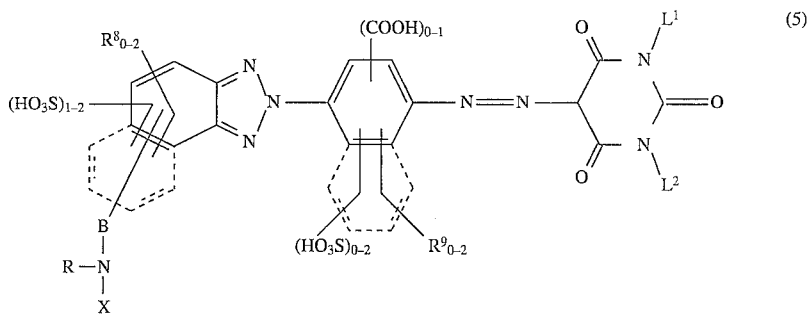

in particular those of the formula (5a)

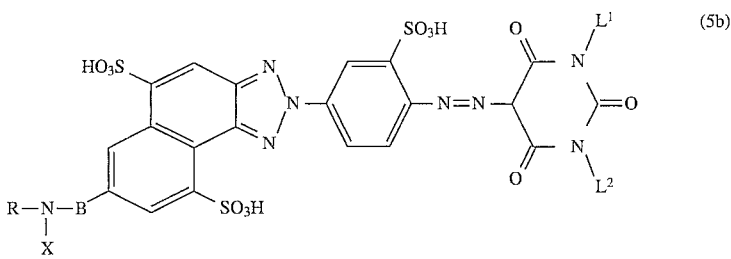

and (5b)

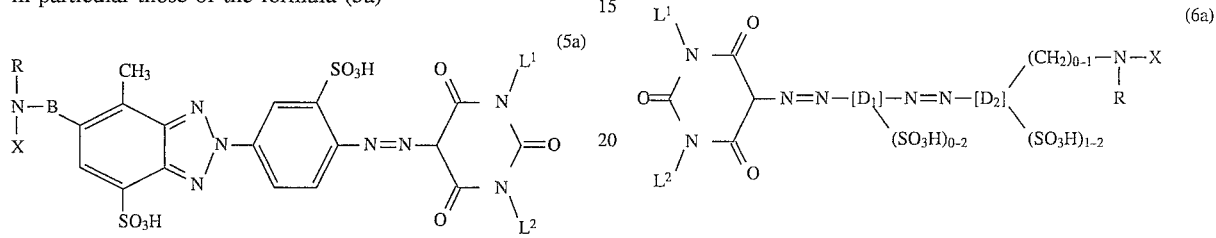

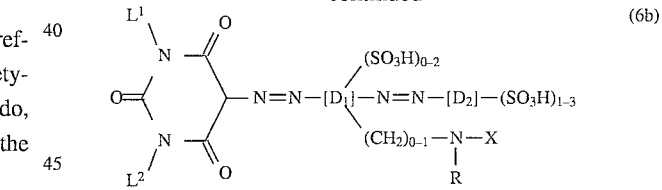

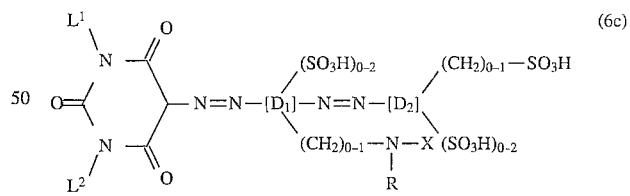

wherein $R^8$ and $R^9$ independently of one another can preferably be hydrogen, $C_1$–$C_4$-alkyl, $C_1$–$C_4$-alkoxy, acetylamino, $NH_2$, methylamino, ethylamino, carbamoyl, ureido, hydroxyl or acetyl and the other substituents have the meanings given under formula (1).

Dyestuffs which are likewise preferred are those of the formula (6)

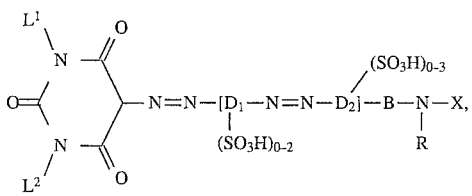

wherein $D_1$ and $D_2$ independently of one another denote a phenylene or naphthylene radical, which can be substituted by $C_1$–$C_4$-alkyl, $C_1$–$C_4$-alkoxy, $CO_2H$, $NHCO$-$C_1$–$C_4$-alkyl, $NHCONH_2$ or halogen, in particular Cl or F, and B, R and X have the abovementioned meanings.

Particularly preferred dyestuffs of the formula (6) are those of the formulae (6a), (6b) and (6c)

wherein $D_1$, $D_2$, R and X have the above meanings.

Dyestuffs of the formula (1) which are furthermore preferred are those which correspond to the formula (7)

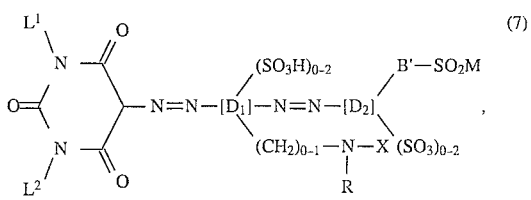

wherein $D_1$ and $D_2$ independently of one another denote a phenylene or naphthalene radical, which can be substituted by $C_1-C_4$-alkyl, $C_1-C_4$-alkoxy, $CO_2H$,

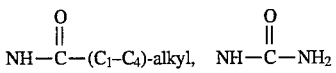

or halogen, in particular Cl or F, and $L^1$, $L^2$, M, B', R and X have the above meanings.

Particularly preferred dyestuffs of the formula (1) are those wherein:

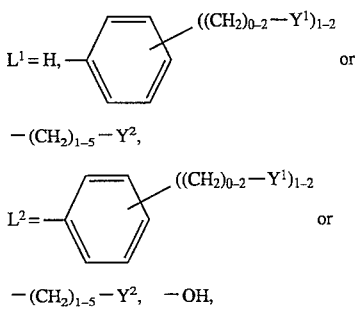

$Y^1$=independently of one another in $L^1$ and $L^2$: OH, COOH, $SO_3H$, $C_1-C_4$-alkoxy, hydroxy-$C_{1-4}$-alkoxy, HO—$(CH_2-CH_2-O)_{1-3}$—, HOOC—$(CH_2-CH_2-O)_{1-3}$—, $HO_3S$—$(CH_2-CH_2-O)_{1-3}$—, $HO_3S$—$CH_2-CH_2-CH_2-O$—, or HOOC—$CH_2-CH_2-CH_2-O$—, and $Y^2$=independently of one another in $L^1$ and $L^2$: OH, COOH, $OSO_3H$, $SO_3H$, $C_1-C_4$-alkoxy, hydroxy-$C_{1-4}$-alkoxy, HO—$(CH_2-CH_2-O)_{1-3}$—, HOOC—$(CH_2-CH_2-O)_{1-3}$—, $HO_3S$—$(CH_2-CH_2-O)_{1-3}$—, $HO_3S$—$CH_2-CH_2-CH_2-O$—, HOOC—$CH_2-CH_2-CH_2-O$— or

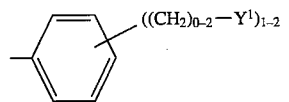

Especially preferred dyestuffs of the formula I are those wherein:

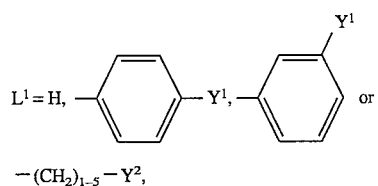

$Y^2$ = OH, $OSO_3H$, COOH, $SO_3H$ or

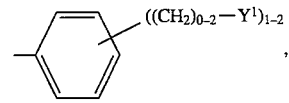, $Y^1$ = OH, COOH or $SO_3H$.

Preferred meanings for D, $D_1$ and $D_2$ are derived, for example, from the following diazo components:

1,3-diaminobenzene, 1,4-diaminobenzene, 1,3-diamino-4-chlorobenzene, 1,3-diamino-4-methylbenzene, 1,3-diamino-4-ethylbenzene, 1,3-diamino-4-methoxybenzene, 1,3-diamino-4-ethoxybenzene, 1,4-diamino-2-methylbenzene, 1,4-diamino-2-methoxybenzene, 1,4-diamino-2-ethoxybenzene, 1,4-diamino-2-chlorobenzene, 1,4-diamino-2,5-dimethylbenzene, 1,4-diamino-2,5-diethylbenzene, 1,4-diamino-2-methyl-5-methoxybenzene, 1,4-diamino-2,5-dimethoxybenzene, 1,4-diamino-2,5-diethoxybenzene, 2,6-diamino-naphthalene, 1,3-diamino-2,4,6-trimethylbenzene, 1,4-diamino-2,3,5,6-tetramethylbenzene, 1,3-diamino-4-nitrobenzene, 4,4'-diaminostilbene, 4,4'-diaminodiphenylmethane, 4,4'-diaminobiphenyl (benzidine), 3,3'-dimethylbenzidine, 3,3'-dimethoxybenzidine, 3,3'-dichlorobenzidine, 3,3'-dicarboxybenzidine, 3,3'-dicarboxymethoxy-benzidine, 2,2'-dimethylbenzidine, 4,2'-diaminodiphenyl (diphenyline), 2,6-diaminonaphthalene-4,8-disulphonic acid, 1,4-diaminobenzene-2-sulphonic acid, 1,4-diaminobenzene-2,5-disulphonic acid, 1,4-diaminobenzene-2,6-disulphonic acid, 1,3-diaminobenzene-4-sulphonic acid, 1,3-diaminobenzene-4,6-disulphonic acid, 1,4-diamino-2-chlorobenzene-5-sulphonic acid, 1,4-diamino-2-methylbenzene-5-sulphonic acid, 1,5-diamino-6-methylbenzene-3-sulphonic acid, 1,3-diamino-6-methylbenzene-4-sulphonic acid, 3-(3'- or 4'-aminobenzoylamino)-1-aminobenzene-6-sulphonic acid, 1-(4'-aminobenzoylamino)-4-aminobenzene-2,5-disulphonic acid, 1,4-diaminobenzene-2-carboxylic acid, 1,3-diaminobenzene-4-carboxylic acid, 1,2-diaminobenzene-4-carboxylic acid, 1,3-diaminobenzene-5-carboxylic acid, 1,4-diaminobenzene-2-methylbenzene, 4,4'-diaminodiphenyl oxide, 4,4'-diaminodiphenylurea-2,2'-disulphonic acid, 4,4'-diaminodiphenyloxyethane-2,2'-disulphonic acid, 4,4'-diaminostilbene-2,2'-disulphonic acid, 4,4'-diaminodiphenylethane-2,2'-disulphonic acid, 2-amino-5-aminomethylnaphthalene-1-sulphonic acid, 2-amino-5-aminomethylnaphthalene-1,7-disulphonic acid, 1-amino-4-methoxy-5-aminomethylbenzene-6-sulphonic acid, 1-amino-4-methyl-5-aminomethylbenzene-6-sulphonic acid.

Suitable coupling components on which the formula 1 is based can be, preferably:

1-Carboxymethylbarbituric acid
1-(2-Carboxyethyl)barbituric acid
1-(3-Carboxypropyl)barbituric acid
1-(5-Carboxypentyl)barbituric acid
1-(2-Hydroxyethyl)barbituric acid
1-(3-Hydroxypropyl)barbituric acid
1-(4-Hydroxybutyl)barbituric acid
1-Sulphomethylbarbituric acid
1-(2-Sulphoethyl)barbituric acid
1-(3-Sulphophenyl)barbituric acid
1-(4-Sulphophenyl)barbituric acid 1,3-bis-(2-Hydroxyethyl)barbituric acid
1,3-bis-(2-Carboxymethyl)barbituric acid
1,3-bis-(2-Carboxyethyl)barbituric acid
1,3-bis-(3-Sulphophenyl)barbituric acid
1-Carboxymethyl-3-(2-hydroxyethyl)barbituric acid
1-(3-Sulphopropyl)barbituric acid
1-(2-Sulphatoethyl)barbituric acid
1,3-bis-(2-Sulphatoethyl)barbituric acid Preferred meanings for B and B' are, independently of one another, a direct bond or a bridge member of the formulae

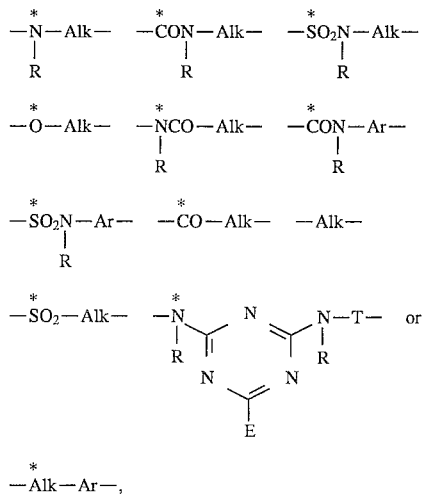

wherein the asterisk marks the linking point with a benzene or naphthalene radical and wherein Alk denotes straight-chain or branched $C_1$–$C_6$-alkylene which is optionally interrupted by heteroatoms or groupings containing heteroatoms such as N, O or S, Ar denotes optionally substituted phenylene or naphthylene or the radical of a diphenyl or stilbene, T denotes Alk or Ar or —Alk—Ar— wherein Alk or Ar are optionally substituted by F, Cl, Br, $C_1$–$C_4$-alkyl, $C_1$–$C_4$-alkoxy, carboxyl or sulpho, and E denotes F, Cl, Br, optionally substituted amino, OH, $C_1$–$C_4$-alkoxy, optionally substituted phenoxy or $C_1$–$C_4$-alkylthio.

Suitable fibre-reactive radicals X, that is to say those which react with the OH or NH groups of the fibre under dyeing conditions to form covalent bonds, are, in particular, those which contain at least one reactive substituent bonded to a 5- or 6-membered aromatic-heterocyclic ring, for example to a monoazine, diazine or triazine ring, in particular a pyridine, pyrimidine, pyridazine, pyrazine, thiazine, oxazine or asymmetric or symmetric triazine ring, or to such a ring system which contains one or more fused-on aromatic-carbocyclic rings, for example a quinoline, phthalazine, cinnoline, quinazoline, quinoxaline, acridine, phenazine and phenanthridine ring system.

Fibre-reactive radicals from the series comprising pyrimidines and triazines are particularly suitable here.

Examples of the reactive substituents on the heterocyclic radical which may be mentioned are halogen (Cl, Br or F), ammonium, including hydrazinium, pyridinium, picolinium, carboxypyridinium, sulphonium, sulphonyl, azido ($N_3$), thiocyanato, thiol ether, oxyether, sulphinic acid and sulphonic acid.

X can accordingly in particular represent

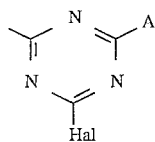

wherein
Hal=Cl or F and
A=the radical of an amine AH, preferred compounds AH being:

ammonia, methylamine, ethylamine, n-propanolamine, iso-propanolamine, n-butylamine, iso-butylamine, tert-butylamine, n-pentylamine, n-hexylamine, cyclohexylamine, dimethylamine, diethylamine, di-n-propylamine, di-isopropylamine, methylethylamine, ethanolamine, diethanol amine, 2-methoxyethylamine, 2-ethoxyethylamine, sulphatoethylamine, aminoacetic acid, N-methylaminoacetic acid, taurine, N-methyltaurine, methylaminomethanesulphonic acid, pyrrolidine, piperidine, 1-methyl-piperazine, morpholine, benzylamine β-phenylethylamine, N-methylmorpholine, benzylamine, dibenzylamine, aniline, 1-Amino-2-, -3- or -4-methylbenzene, 1-Amino-3,4-, or -3,5-dimethylbenzene, 1-Amino-2 -, -3- or -4-ethylbenzene, 1-Amino-2-, -3- or -4-methoxybenzene, 1-Amino -4-ethoxybenzene, 1-Amino-2-, -3- or -4-(2-hydroxyethoxy)-benzene, 1-Amino-2-, -3- or -4-(2-methoxyethoxy)-benzene, 1-Amino-2 -, -3- or -4-chlorobenzene, 2-, 3- or 4-Amino-phenylmethanesulphonic acid, 2-Aminobenzenesulphonic acid, 3-Aminobenzenesulphonic acid, 4-Aminobenzenesulphonic acid, 5-Aminobenzene-1,3- or -1,4-disulphonic acid, 4-Aminobenzene-1,2- or -1,3-disulphonic acid, 2-, 3- or 4-Aminobenzenesulphonamide, 2-, 3- or 4-Aminobenzenesulphonic acid methylamide, 2-, 3- or 4-Aminobenzenesulphonic acid dimethylamide, 2-, 3- or 4-Aminobenzenesulphonic acid (2-hydroxyethyl)amide, 5-Aminobenzene-1,3-dicarboxylic acid, 2-, 3- or 4-Aminobenzoic acid, 2-, 3- or 4-Aminobenzamide, Methyl or ethyl 2-, 3- or 4-aminobenzoate, 2-, 3- or 4-Aminobenzonitrile, 3-Amino-(N-phenylsulphonyl)-benzenesulphonamide, 2-, 3- or 4-Aminophenol, 5-Amino-2-hydroxybenzenesulphonic acid, 4-Amino-2-hydroxybenzenesulphonic acid, 5-Amino-2-ethoxybenzenesulphonic acid, 1-acetylamino-2-, or -4-aminobenzene, 1-Amino-3-, or -4-(hydroxyacetyl)-aminobenzene, 1-Amino-4-(sulphoacetyl)-aminobenzene, 3- or 4-Aminophenylurea, N-(3-Aminophenyl)-N'-(2-hydroxyethyl)-urea, 3- or 4-Aminophenyloximidic acid, 1-Methylamino-3- or -4-methylbenzene, 1-Ethylamino-4-chlorobenzene, 2-Amino-5-methoxy-benzenesulphonic acid, 3-Amino-4-methoxy-benzenesulphonic acid, 1-Ethylamino-3- or -4-methylbenzene, N-(2-Hydroxyethyl)-aniline, 1-(2-Hydroxyethyl)-amino-3-methylbenzene, 3- or 4-Methylaminobenzoic acid, 4-Methylaminobenzenesulphonic acid, 5-Amino-2-oxalamino-benzenesulphonic acid, 2-Aminonaphthalene-1-sulphonic acid, 4-Aminonaphthalene-1-sulphonic acid, 5-Aminonaphthalene-1-sulphonic acid, 6-Aminonaphthalene-1-sulphonic acid, 7-Aminonaphthalene-1-sulphonic acid, 8-Aminonaphthalene-1-sulphonic acid, 1-Aminonaphthalene-2-sulphonic acid, 4-Aminonaphthalene-2-sulphonic acid, 5-Aminonaphthalene-2-sulphonic acid, 6-Aminonaphthalene-2-sulphonic acid, 7-Aminonaphthalene-2-sulphonic acid, 7-Methylaminonaphthalene-2-sulphonic acid 7-Butylaminonaphthalene-2-sulphonic acid 7-Isobutylaminonaphthalene-2-sulphonic acid 8-Aminonaphthalene-1-sulphonic acid, 4-Aminonaphthalene-1,3-disulphonic acid, 5-Aminonaphthalene-1,3-disulphonic acid, 6-Aminonaphthalene-1,3-disulphonic acid, 7-Aminonaphthalene-1,3-disulphonic acid, 8-Aminonaphthalene-1,3-disulphonic acid, 2-Aminonaphthalene-1,5-disulphonic acid, 3-Aminonaphthalene-1,5-disulphonic acid, 4-Aminonaphthalene-1,5-disulphonic acid, 4-Aminonaphthalene-1,6-disulphonic acid, 8-Aminonaphthalene-1,6-disulphonic acid, 4-Aminonaphthalene-1,7-disulphonic acid, 3-Aminonaphthalene-2,6-disulphonic acid, 4-Aminonaphthalene-2,6-disulphonic acid, 3-Aminonaphthalene-2,7-disulphonic acid, 4-Aminonaphthalene-2,7-disulphonic acid, 6-Aminonaphthalene-1,3,5-trisulphonic acid, 7-Aminonaphthalene-1,3,5-trisulphonic acid, 8-Aminonaphthalene-1,3,5-trisulphonic acid, 4-Aminonaphthalene-1,3,6-trisulphonic acid, 7-Aminonaphthalene-1,3,6-trisulphonic acid, 8-Aminonaphthalene-1,3,6-trisulphonic acid, 4-Aminonaphthalene-1,3,7-trisulphonic acid.

The radical X is preferably a halogenotriazinyl radical, which can also be linked to a second halogenotriazinyl radical or a halogenotriazinyl radical or one or more vinylsulphonyl or sulphatoethylsulphonyl radicals, directly or via a bridge member. Corresponding bridge members are preferably:

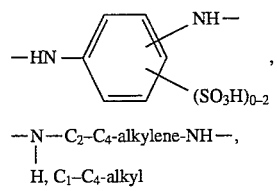

$$-N-C_2-C_4\text{-alkylene-NH}-,$$
$$\mid$$
$$H, C_1-C_4\text{-alkyl}$$

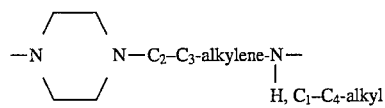

or in the case of the sulphatoethylsulphonyl or vinylsulphonyl sulphonyl group, via a bridge member

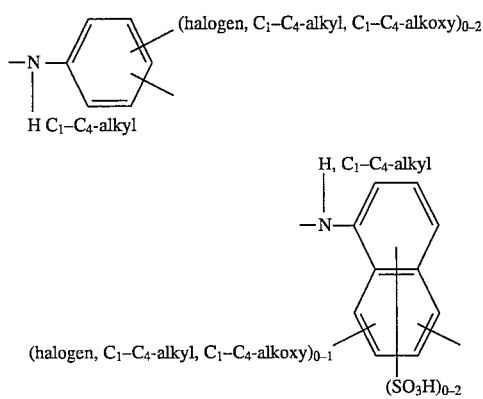

In these formulae, the alkyl radicals can in turn be substituted, in particular by $SO_3H$, $COOH$, $OH$ or $OSO_3H$.

Examples of such radicals X are:

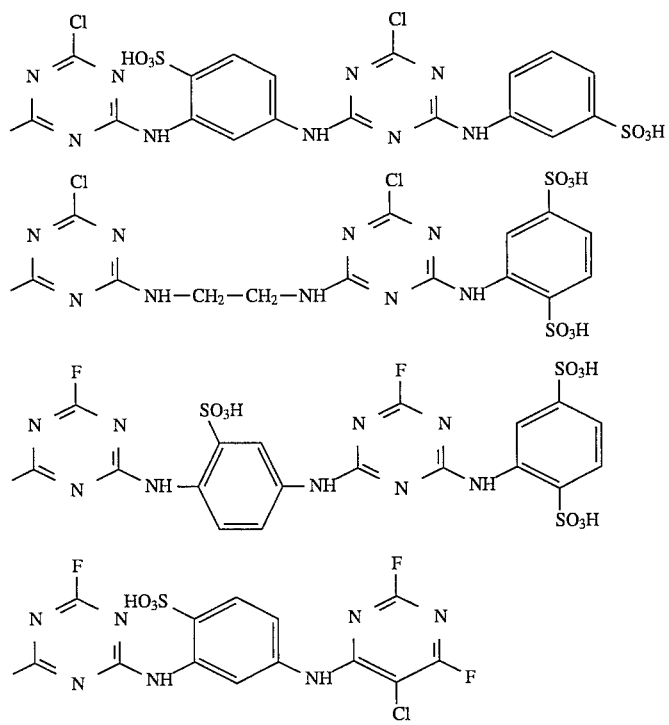

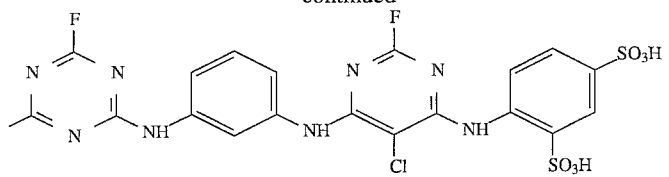
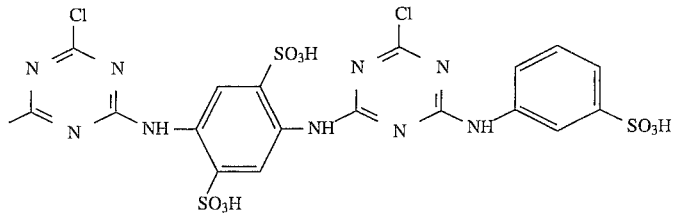
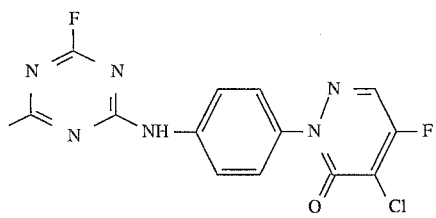
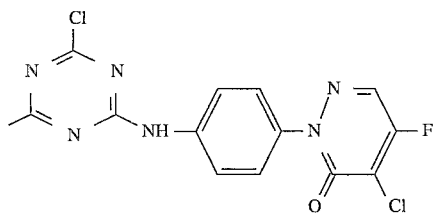
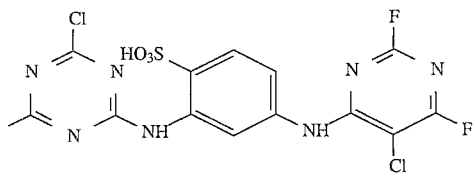
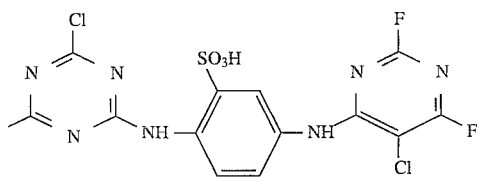
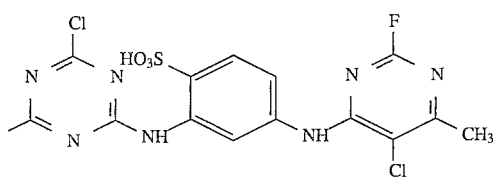
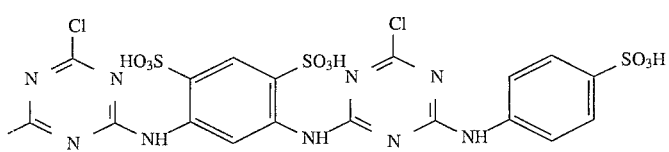

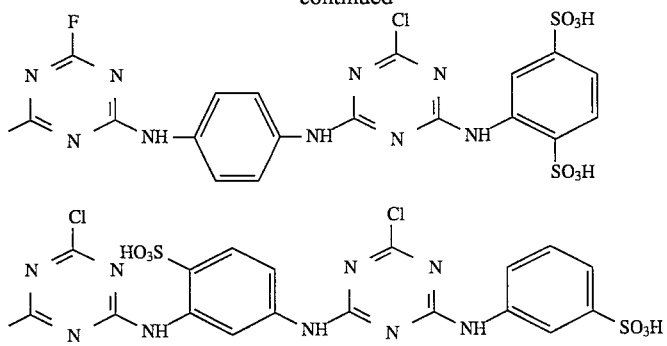

Other examples of X are: mono-, di- or trihalogenopyrimidinyl radicals, such as 2,4-dichloropyrimidin-6-yl, 2,4,5-trichloropyrimidin-6-yl, 2,4-dichloro-5-nitro- or -5-methyl or -5-carboxymethyl- or -5-carboxy- or -5-cyano- or -5-vinyl- or -5-sulpho- or -5-mono-, -di- or -trichloromethyl- or -5-carbalkoxy-pyrimidin-6-yl, 2,6-dichloropyrimidine-4-carbonyl, 2,4-dichloropyrimidine-5-carbonyl, 2-chloro-4-methylpyrimidine-5-carbonyl, 2-methyl-4-chloropyrimidine-5-carbonyl, 2-methylthio-4-fluoropyrimidine-5-carbonyl, 6-methyl-2,4-dichloropyrimidine-5-carbonyl, 2,4,6-trichloropyrimidine-5-carbonyl, 2,4-dichloropyrimidine-5-sulphonyl, 2-chloro-quinoxaline-3-carbonyl, 2- or 3-monochloroquinoxaline-6-carbonyl, 2- or 3-monochloroquinoxaline- 6-sulphonyl, 2,3-dichloroquinoxaline-5- or -6-carbonyl, 2,3-dichloroquinoxaline-5- or -6-sulphonyl, 1,4-dichlorophthalazine-6-sulphonyl or -6-carbonyl, 2,4-dichloroquinazoline-7- or -6-sulphonyl or -carbonyl, 2- or 3- or 4-(4',5'-dichloropyridaz-6'-on-1'-yl)-phenylsulphonyl or -carbonyl, β-(4',5'-dichloropyridaz-6'-on-1'-yl)-ethylcarbonyl, N-methyl-N-(2,3-dichloroquinoxaline-6-sulphonyl)-aminoacetyl, N-methyl-N-(2,3-dichloro-quinoxaline-6-carbonyl)-aminoacetyl, and the corresponding bromine and fluorine derivatives of the abovementioned chlorine-substituted heterocyclic radicals, and among these, for example, 2-fluoro-4-pyrimidinyl, 2,6-difluoro-4-pyrimidinyl, 2,6-difluoro-5-chloro-4-pyrimidinyl, 2-fluoro-5,6-dichloro-4-pyrimidinyl, 2,6-difluoro-5-methyl-4-pyrimidinyl, 2-fluoro-5-methyl-6-chloro-4-pyrimidinyl, 2-fluoro-5-nitro-6-chloro-4-pyrimidinyl, 5-bromo-2-fluoro-4-pyrimidinyl, 2-fluoro-5-cyano-4-pyrimidinyl, 2-fluoro-5-methyl-4-pyrimidinyl, 2,5,6-trifluoro-4-pyrimidinyl, 5-chloro-6-chloromethyl-2-fluoro-4-pyrimidinyl, 5-chloro-6-dichloromethyl-2-fluoro-4-pyrimidinyl, 5-chloro-6-trichloromethyl-2-fluoro-4-pyrimidinyl, 5-chloro-2-chloromethyl-6-fluoro-4-pyrimidinyl, 5-chloro-2-dichloromethyl-6-fluoro-4-pyrimidinyl, 5-chloro-2-trichloromethyl-6-fluoro-4-pyrimidinyl, 5-chloro-2-fluoro-dichloromethyl-6-fluoro-4-pyrimidinyl, 2,6-difluoro-5-bromo-4-pyrimidinyl, 2-fluoro-5-bromo-6-methyl-4-pyrimidinyl, 2-fluoro-5-bromo-6-chloromethyl-4-pyrimidinyl, 2,6-difluoro-5-chloromethyl-4-pyrimidinyl, 2,6-difluoro-5-nitro-4-pyrimidinyl, 2-fluoro-6-methyl-4-pyrimidinyl, 2-fluoro-5-chloro-6-methyl-4-pyrimidinyl, 2-fluoro-6-chloro-4-pyrimidinyl, 6-trifluoromethyl-5-chloro-2-fluoro-4-pyrimidinyl, 6-trifluoromethyl-2-fluoro-4-pyrimidinyl, 2-fluoro-5-nitro-4-pyrimidinyl, 2-fluoro-5-trifluoromethyl-4-pyrimidinyl, 2-fluoro-5-phenyl- or -5-methylsulphonyl-4-pyrimidinyl, 2-fluoro-5-carboxamido-4-pyrimidinyl, 2-fluoro-5-bromo-6-trifluoromethyl-4-pyrimidinyl, 2-fluoro-6-carboxamido-4-pyrimidinyl, 2-fluoro-6-carbomethoxy-4-pyrimidinyl, 2-fluoro-6-phenyl-4-pyrimidinyl, 2-fluoro-6-cyano-4-pyrimidinyl, 5-chloro-6-fluoro-2-methyl-4-pyrimidinyl, 5,6-difluoro-2-trifluoromethyl-4-pyrimidinyl, 5-chloro-6-fluoro-2-dichlorofluoromethyl- 4-pyrimidinyl, 2-fluoro-5-chloropyrimidin-4-yl, 2-methyl-4-fluoro-5-methylsulphonylpyrimidin-6-yl, 2,6-difluoro-5-methylsulphonyl-4-pyrimidinyl, 2,6-dichloro-5-methylsulphonyl-4-pyrimidinyl, 2-fluoro-5-sulphonamido-4-pyrimidinyl, 2-fluoro-5-chloro-6-carbomethoxy-4-pyrimidinyl, 2,6-difluoro-5-trifluoromethyl-4-pyrimidinyl; triazine radicals containing sulphonyl groups, such as 2,4-bis-(phenylsulphonyl)-trazin-6-yl, 2-(3'-carboxyphenyl)-sulphonyl-4-chlorotriazin-6-yl, 2-(3'-sulphophenyl)-sulphonyl-4-chlorotriazin-6-yl, 2,4-bis-(3'-carboxyphenylsulphonyl)-trazin-6-yl; pyrimidine rings containing sulphonyl groups, such as 2-carboxymethylsulphonyl-pyrimidin-4-yl, 2-methylsulphonyl-6-methyl-pyrimidin-4-yl, 2-methylsulphonyl-6-ethyl-pyrimidin-4-yl, 2-phenylsulphonyl-5-chloro-6-methyl-pyrimidin-4-yl, 2,6-bis-methylsulphonylpyrimidin-4-yl, 2,6-bis-methylsulphonyl-5-chloropyrimidin-4-yl, 2,4-bis-methylsulphonyl-pyrimidine-5-sulphonyl, 2-methylsulphonyl-pyrimidin-4-yl, 2-phenylsulphonyl-pyrimidin-4-yl, 2-trichloromethylsulphonyl-6-methyl-pyrimidin-4-yl, 2-methylsulphonyl-5-chloro-6-methyl-pyrimidin-4-yl, 2-methylsulphonyl-5-bromo-6 -methyl-pyrimidin-4-yl, 2-methylsulphonyl-5-chloro-6-ethyl-pyrimidin-4-yl, 2-methylsulphonyl-5-chloro-6-chloromethyl-pyrimidin-4-yl, 2-methylsulphonyl-4-chloro-6-methyl-pyrimidine-5-sulphonyl, 2-methylsulphonyl-5-nitro-6-methylpyrimidin-4-yl, 2,5,6-tris-methylsulphonyl-pyrimidin-4-yl, 2-methylsulphonyl-5,6-dimethyl-pyrimidin-4-yl, 2-ethylsulphonyl-5-chloro-6-methyl-pyrimidin-4-yl, 2-methylsulphonyl-6-chloro-pyrimidin-4-yl, 2,6-bis-methylsulphonyl-5-chloropyrimidin-4-yl, 2-methylsulphonyl-6-carboxypyrimidin-4-yl, 2-methylsulphonyl-5-sulpho-pyrimidin-4-yl, 2-methylsulphonyl-6-carbomethoxy-pyrimidin-4-yl, 2-methylsulphonyl-5-carboxy-pyrimidin-4-yl, 2-methylsulphonyl-5-cyano-6-methoxy-pyrimidin-4-yl, 2-methylsulphonyl-5-chloro-pyrimidin-4-yl, 2-β-sulphoethylsulphonyl-6-methyl-pyrimidin-4-yl, 2-methylsulphonyl-5-bromo-pyrimidin-4-yl, 2-phenylsulphonyl-5-chloropyrimidin-4-yl, 2-methylsulphonyl-6-chloropyrimidine-4- and -5-carbonyl, 2,6-bis-(methylsulphonyl)-pyrimidine-4- or -5-carbonyl, 2-ethylsulphonyl-6-chloropyrimidine-5-carbonyl, 2,4 -bis-(methylsulphonyl)-pyrimidine-5-sulphonyl, 2-methylsulphonyl-4-chloro-6 -methylpyrimidine-5-sulphonyl or -carbonyl; 2-chlorobenzothiazole-5- or -6-carbonyl or -5- or -6-sulphonyl, 2-arylsulphonyl- or -alkylsulphonylbenzothiazole-5- or -6-carbonyl or -5- or -6-sulphonyl, such as 2-methylsulphonyl- or 2-ethylsulphonyl-benzothiazole-5 - or -6-sulphonyl or carbonyl, 2-phenylsulphonylbenzothiazole-5- or -6-sulphonyl or -carbonyl and the corresponding 2-sulphonylbenzothiazole-5- or -6-carbonyl or -sulphonyl derivatives containing sulpho groups in the fused-on benzene ring, 2-chlorobenzoxazole-5- or -6-carbonyl or -sulphonyl, 2-chlorobenzimidazole-5- or -6-carbonyl or -sulphonyl, 2-chloro-1-methylbenzimidazole-5- or -6-carbonyl or -sulphonyl, 2-chloro-4-methyl-1,3-thiazole-5-carbonyl or -4- or -5-sulphonyl and the N-oxide of 4-chloro- or 4-nitroquinoline-5-carbonyl.

If X=pyrimidine, those of the formula

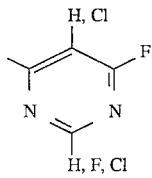

are to be mentioned in particular.

Especially preferred dyestuffs of the formula (1) are those wherein

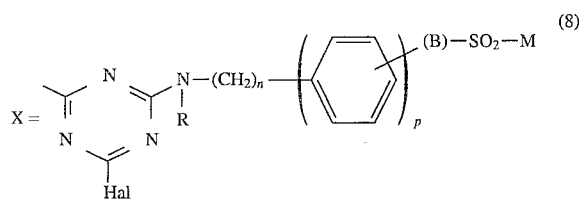

where n=0–3; p=0–1; B=—(CH$_2$)$_m$— or (CH$_2$)$_2$—O—(CH$_2$)$_2$; m=0–6; Hal=Cl or F and R and M have the above meanings, the following being mentioned in particular Hal=Cl or F R=phenyl; n=0; p=0; m=2, or R=H; n=0; p=1; m=1, wherein the phenyl ring between the

and —CH$_2$—SO$_2$M meta-substituted,

R=H; n=0; p=0; m=3 or

R=H; n=0; p=1 (para); m=0, where the phenylene ring between

and —SO$_2$M is para-substituted,

R=H; n=0; B=—(CH$_2$)$_2$—O—(CH$_2$)$_2$—.

Dyestuffs of the formula (1) which are furthermore especially preferred are those wherein

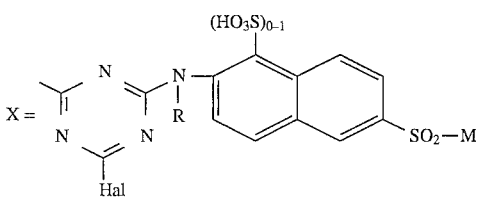

or

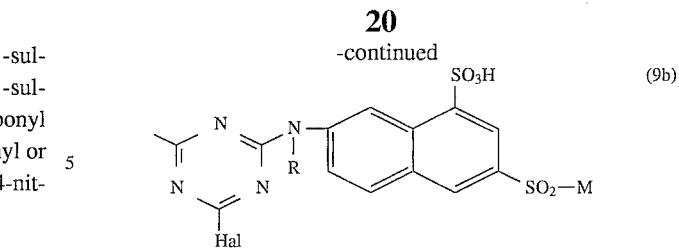

where, preferably,

Hal=Cl or F,

R=H and

M=the meaning given under formula (1).

Preferred diazo components are the triazoles described in DE-A-2,208,972, EP-A-0,088,930 and EP-A-0,013,879. These can be employed as reactive diazo components or can be reacted only after coupling with the reactive anchor.

The invention furthermore relates to a process for the preparation of the dyestuffs (1), characterized in that compounds of the formula (10)

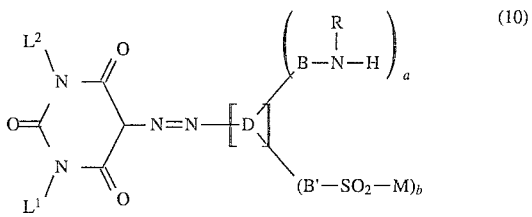

or the corresponding diazo components of the formula

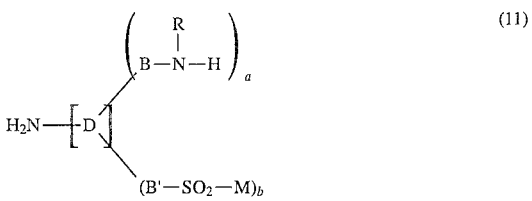

wherein a=0, 1 or 2; b=0, 1 or 2 and a+b=1 or 2 and the other substituents have the above meanings, are reacted with 1 to 2 molar equivalents of a reactive component of the formula X—Hal, wherein X denotes a fibre-reactive heterocyclic radical and Hal represents halogen, in particular F and Cl, and, if precursors are used, these are then converted into the desired end dyestuffs, and if appropriate further conversion reactions are subsequently carried out.

In the preparation of preferred azo dyestuffs, the diazo component must contain two amino groups or one amino group and a reactive radical —SO$_2$M or a precursor of the radical —SO$_2$M. The diazo components can optionally contain further acylatable amino groups. Corresponding acylamino or nitro compounds wherein the acylamino or nitro group is converted into the NH$_2$ group by hydrolysis or reduction before condensation with a halogenotriazine, halogenopyrimidine or the like are used, if appropriate. The reactive radical X is introduced by condensation of dyestuffs or dyestuff precursors which contain acylatable amino groups with fibre-reactive halogenated acylating agents. The preparation of end dyestuffs from precursors usually involves coupling reactions which lead to azo dyestuffs.

Since the individual process steps mentioned above can be carried out in different sequences, various process variants are possible. In general, the reaction is carried out stepwise in succession, the sequence of the simple reactions between the individual reaction components advantageously depending on the particular conditions. Since hydrolysis of the reactive radical occurs under certain preconditions, an intermediate product which contains acylamino groups must be hydrolysed, for the purpose of splitting off the acyl groups, before condensation is carried out with an aminodifluorotriazine or trifluorotriazine and the like. A possible further conversion reaction is, for example, subsequent reaction of a dihalogenotriazinyl radical with an amine. The most important process variants are described in the embodiment examples.

Suitable starting compounds for the preparation of mono- or polyazo dyestuffs (1) are, for example:

Diazo Components 1,3-diaminobenzene, 1,4-diaminobenzene, 1,3-diamino-4-chlorobenzene, 1,3-diamino-4-methylbenzene, 1,3-diamino-4-ethylbenzene, 1,3-diamino-4-methoxybenzene, 1,3-diamino-4-ethoxybenzene, 1,4-diamino-2-methylbenzene, 1,4-diamino-2-methoxybenzene, 1,4-diamino-2-ethoxybenzene, 1,4-diamino-2-chlorobenzene, 1,4-diamino-2,5-dimethylbenzene, 1,4-diamino-2,5-diethylbenzene, 1,4-diamino-2-methyl-5-methoxybenzene, 1,4-diamino-2,5-dimethoxybenzene, 1,4-diamino-2,5-diethoxybenzene, 2,6-diamino-naphthalene, 1,3-diamino-2,4,6-trimethylbenzene, 1,4-diamino-2,3,5,6-tetramethylbenzene, 1,3-diamino-4-nitrobenzene, 4,4'-diaminostilbene, 4,4'-diaminodiphenylmethane, 4,4'-diaminobiphenyl (benzidine), 3,3'-dimethylbenzidine, 3,3'-dimethoxybenzidine, 3,3'-dichlorobenzidine, 3,3'-dicarboxybenzidine, 3,3'-dicarboxymethoxy-benzidine, 2,2'-dimethylbenzidine, 4,2'-diaminodiphenyl (diphenyline), 2,6-diaminonaphthalene-4,8-disulphonic acid, 1,4-diaminobenzene-2-sulphonic acid, 1,4-diaminobenzene-2,5-disulphonic acid, 1,4-diaminobenzene-2,6-disulphonic acid, 1,3-diaminobenzene-4-sulphonic acid, 1,3-diaminobenzene-4,6-disulphonic acid, 1,4-diamino-2-chlorobenzene-5-sulphonic acid, 1,4-diamino-2-methylbenzene-5-sulphonic acid, 1,5-diamino-6-methylbenzene-3-sulphonic acid, 1,3-diamino-6-methylbenzene-4-sulphonic acid, 3-(3'- or -4'-aminobenzoylamino)-1-aminobenzene-6-sulphonic acid, 1-(4'-aminobenzoylamino)-4-aminobenzene-2,5-disulphonic acid, 1,4-diaminobenzene-2-carboxylic acid, 1,3-diaminobenzene-4-carboxylic acid, 1,2-diaminobenzene-4-carboxylic acid, 1,3-diaminobenzene-5-carboxylic acid, 1,4-diaminobenzene-2-methylbenzene, 4,4'-diaminodiphenyl oxide, 4,4'-diaminodiphenylurea-2,2'-disulphonic acid, 4,4'-diaminodiphenyloxyethane-2,2'-disulphonic acid, 4,4'-diaminostilbene-2,2'-disulphonic acid, 4,4'-diaminodiphenylethane-2,2'-disulphonic acid, 2-amino-5-aminomethylnaphthalene-1-sulphonic acid, 2-amino-5-aminomethylnaphthalene-1,7-disulphonic acid, 1-amino-4-methoxy-5-aminomethylbenzene-6-sulphonic acid, 1-amino-4-methyl-5-aminomethylbenzene-6-sulphonic acid.

If an amino-acetylamino compound from which the acyl group is subsequently split off again by hydrolysis is to be employed as the diazo component instead of a diamine, as is described above in the explanations of the process variants, the monoacyl compounds of the abovementioned diazo components are suitable, for example 1-acetylamino-3-aminobenzene-4-sulphonic acid or 1-acetylamino-4-aminobenzene-3-sulphonic acid.

The diazotization of the diazo components and of the intermediate products containing a diazotizable amino group is as a rule carried out by the action of nitrous acid in aqueous mineral acid solution at a low temperature. Coupling to the coupling component is carried out at strongly acid, neutral to weakly alkaline pH values.

Coupling components of the formula

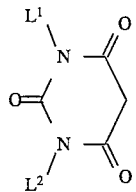

are known in some cases from P. L. Southwick, A. S. Wagman and A. S. Waggoner, Org. Prep. Proced. Int. 23 (1991) 6, 713; P. L. Southwick and A. S. Waggoner, Org. Prep. Proced. Int. 21 (1989) 4, 493; DOS 1,925,559 and DOS 2,711,450, or can be prepared analogously.

The condensation of the reactive components with the diazo components and with the amines or with acylatable monoazo or disazo intermediate products or with the dyestuffs containing amino groups is preferably carried out in aqueous solution or suspension, at a low temperature and at a weakly acid, neutral to weakly alkaline pH.

The hydrogen halide liberated during the condensation is advantageously neutralized continuously by addition of aqueous alkali metal hydroxides, carbonates or bicarbonates.

The formulae given are those of the free acids. The salts, in particular the alkali metal salts, such as sodium, potassium or lithium salts, are in general obtained in the preparation. The charge formed by quaternization with pyridines is compensated by a counter-ion, for example chloride, fluoride or sulphate, depending on the isolation conditions; alternatively, the dyestuffs form inner salts with sulpho or carboxyl groups.

All the dyestuffs, in particular those which are reacted with pyridines in the last stage, can be in the form of mixtures of the β-sulphatoethylsulphonyl dyestuffs and the eliminated form thereof with the vinyl sulphone. The dyestuffs can also be employed as concentrated solutions.

The dyestuffs according to the invention are outstandingly suitable for dyeing and printing naturally occurring and synthetic materials containing OH or amide groups, in particular those of cellulose and polyamides. They are particularly suitable for dyeing cellulose materials by the exhaust and cold pad-batch process, and for printing cotton and cellulose.

Dyeings with good general fastnesses, in particular wet-fastness properties, coupled with a good build-up capacity and high fixing yields, are obtained.

The present invention likewise relates to compounds of the formula (12)

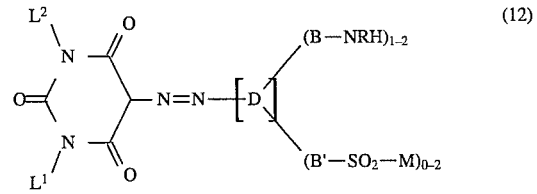

wherein $L^1$, $L^2$, B, B', R, D and M have the abovementioned meanings.

These are useful intermediate products for the preparation of the reactive dyestuffs of the formula (1).

Preferred compounds of the formula (12) are those in which the substituents have the above preferred meanings.

Dyeing instructions The dyeings described in the following examples are carried out under the following conditions:

Dyeing Instructions 1

2 parts of the dyestuff are dissolved in 100 ml of water. The solution is added to 1900 parts of cold water, 60 parts of sodium chloride are added and 100 parts of a cotton fabric are introduced into this dyebath.

The temperature is increased to 60° C., 40 parts of calcined sodium carbonate and a further 60 parts of sodium chloride being added after 30 minutes. The temperature is kept at 60° C. for 30 minutes and the dyeing is then rinsed and soaped in a 0.3% strength boiling solution of an ion-free detergent for 15 minutes, rinsed and dried.

Dyeing Instructions 2

4 parts of the reactive dyestuff are dissolved in 50 parts of water. 50 parts of a solution containing 5 g of sodium hydroxide and 10 g of calcined sodium carbonate per liter are added to the solution. A cotton fabric is padded with the resulting solution such that it increases by 70% of its weight, and is then wound up to a roll of fabric. The cotton fabric is stored in this manner at room temperature for 3 to 12 hours. The dyed goods are then rinsed, soaped at the boil with a non-ionic detergent for a quarter of an hour, rinsed again and dried.

EXAMPLE 1

0.29 mol of 4-(2-sulphatoethyl)sulphonylaniline are diazotized in a known manner and the diazotization product is coupled to 0.29 mol of 1-(2-sulphoethyl)barbituric acid or the mono- or disodium salt at pH 5–7.

The dyestuff of the formula

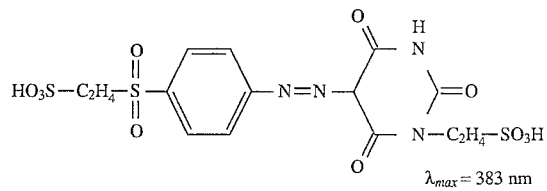

$\lambda_{max} = 383$ nm obtained after salting out, isolation, drying and grinding dyes cotton in greenish-tinged yellow shades.

Further useful greenish-tinged yellow reactive dyestuffs (Examples 2 to 6) are obtained by varying the diazo components and coupling components.

| Example | Diazo component | Coupling component |
|---|---|---|
| 2 | HO$_3$S—O—C$_2$H$_4$—S(O)$_2$-naphthalene-SO$_3$H, NH$_2$ | 1-carboxymethyl-barbituric acid $\lambda_{max} = 394$ nm |
| 3 | HO$_3$S—O—C$_2$H$_4$—S(O)$_2$-naphthalene-SO$_3$H, NH$_2$ | 1-(4-sulpho-phenyl)barbituric acid $\lambda_{max} = 396$ nm |
| 4 | HO$_3$S—O—C$_2$H$_4$—SO$_2$-naphthalene-HO$_3$S, NH$_2$ | 1-(2-sulpho-ethyl)barbituric acid |
| 5 | HO$_3$S—O—C$_2$H$_4$—SO$_2$-naphthalene-HO$_3$S, NH$_2$ | 1-carboxymethyl-barbituric acid |
| 6 | HO$_3$S—O—C$_2$H$_4$—SO$_2$-naphthalene-HO$_3$S, NH$_2$ | 1-(2-hydroxy-ethyl)barbituric acid |

EXAMPLE 7

0.29 mol of 4-acetamino-2-amino-benzosulphonic acid is diazotized in a known manner and the diazotization product is coupled to 0.29 mol of 1-(2-sulphoethyl)barbituric acid at pH 5–7. The product is then hydrolysed in a known manner. The dyestuff of the formula

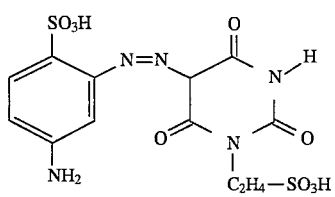

obtained after salting out and isolation can be reacted with any desired heterocyclic reactive hooks.

0.2 mol of the above dyestuff is dissolved in 600 ml of water at pH 7.0 and the solution is cooled to 0° C. with 600 g of ice. 0.21 mol of 2,4,6-trifluoro-1,3,5-triazine (cyanuric fluoride) is added and the pH is kept between 3.5 and 4 with $Na_2CO_3$ solution. After 5 minutes, 0.2 mol of morpholine is added and the pH is brought to 7 with $Na_2CO_3$ solution. During this operation, the temperature rises to about 10° C. The mixture is subsequently stirred at room temperature for 60 minutes. The dyestuff is then salted out, isolated, dried and ground. The dyestuff thus obtained, of the formula

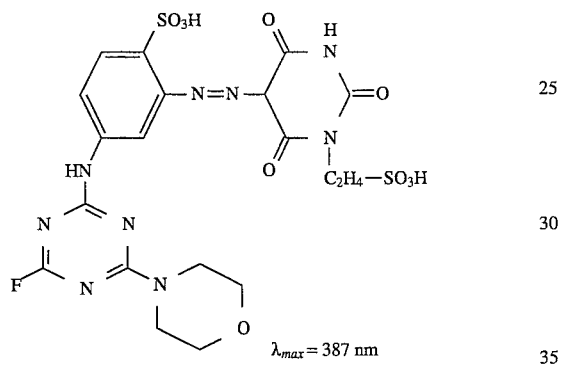

$\lambda_{max} = 387$ nm dyes cotton in clear greenish-tinged yellow shades.

Further useful greenish-tinged yellow reactive dyestuffs of the formula

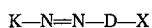

are obtained by varying the diazo components (D), coupling components (K) and reactive hooks.

| Ex. | Diazo component $H_2N-D-X$ | X | Coupling component KH |
|---|---|---|---|
| 8 | SO₃H, NH₂, X—NH (benzene) | F-substituted pyrimidine with Cl | 1-(2-sulpho-ethyl)barbituric acid $\lambda_{max} = 387$ nm |
| 9 | " | HO₃S-phenyl-NH-triazine-F | 1-(2-sulpho-ethyl)barbituric acid $\lambda_{max} = 388$ nm |
| 10 | " | HO₃S-CH₂-CH₂-NH-triazine-F | 1-(2-sulpho-ethyl)barbituric acid $\lambda_{max} = 387$ nm |

-continued

| Ex. | Diazo component H₂N—D—X | X | Coupling component KH |
|---|---|---|---|
| 11 | " | (morpholinyl-substituted triazine with F) | 1-(5-carboxy-pentyl)barbituric acid $\lambda_{max} = 388$ nm |
| 12 | 2-amino-4-(X-NH)-benzenesulfonic acid | 4-(CH₂OSO₃H-CH₂-SO₂-)phenyl-NH-triazine with Cl | 1-carboxymethylbarbituric acid $\lambda_{max} = 388$ nm |
| 13 | 2-amino-5-(HN-X)-benzenesulfonic acid | pyrimidine with F and Cl | 1-(3-sulphophenyl)barbituric acid |
| 14 | " | 3-(OSO₃H-CH₂-CH₂-SO₂-)phenyl-NH-triazine with F | 1-(2-sulphoethyl)barbituric acid |
| 15 | " | 2-SO₃H-4-MeO-phenyl-NH-triazine with F | 1-(2-sulphoethyl)barbituric acid |
| 16 | " | 3-SO₃H-phenyl-NH-triazine with F | 1-(2-sulphoethyl)barbituric acid |
| 17 | 2-amino-5-(HN-X)-benzenesulfonic acid | 4-HO₃S-phenyl-NH-triazine with Cl | 1-(2-sulphoethyl)barbituric acid |
| 18 | 2-amino-4-(HN-CH₂-X)-benzenesulfonic acid | " | 1-(2-sulphoethyl)barbituric acid |

| Ex. | Diazo component $H_2N-D-X$ | X | Coupling component KH |
|---|---|---|---|
| 19 | " | [structure: 2,5-disulfophenyl-NH-C(=N-)-N=C(Cl)-N with triazine] | 1-(2-sulpho-ethyl)barbituric acid |
| 20 | " | [structure: SO₃H-CH₂-CH₂-N(CH₃)-C(=N-)-N=C(Cl)-N triazine] | 1-(2-sulpho-ethyl)barbituric acid |
| 21 | [structure: 2-amino-benzene with SO₃H and CH₃-N(X)-CH₂-] | " | 1-(2-sulpho-ethyl)barbituric acid |
| 22 | [structure: 2-amino-benzene with SO₃H and CH₃-N(X)-CH₂-] | [structure: 2,5-disulfo-4-methoxy-phenyl-NH-C(=N-)-N=C(Cl)-N triazine] | 1-(2-sulpho-ethyl)barbituric acid |
| 23 | " | [structure: HO-CH₂-CH₂-N(phenyl)(3-fluoro-5-methylphenyl)] | 1-(2-sulpho-ethyl)barbituric acid |

EXAMPLE 25

0.29 mol of 2-amino-5-aminomethyl-1-naphthalenesulphonic acid is diazotized in a known manner and the diazotization product is coupled to 0.3 mol of 1-(2-sulphoethyl)barbituric acid. A solution of 0.32 mol of 2-(2',5'-disulphophenyl-amino)- 4,6-dichloro-1,3,5-triazine di-Na salt in 400 ml of water is added to the coupling mixture. The mixture is then heated at 60° C. for 2 hours. The pH is kept at pH=6–7 with sodium carbonate solution.

The dyestuff of the formula

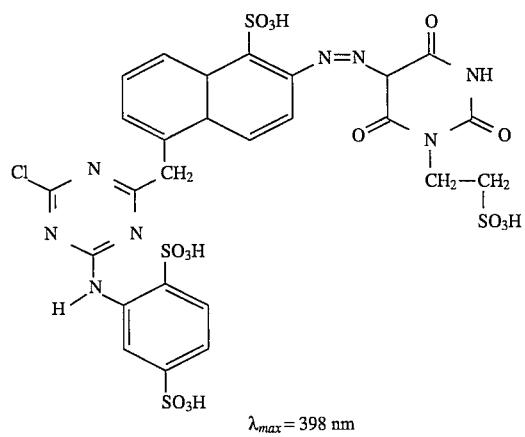

$\lambda_{max} = 398$ nm obtained after salting out, isolation, drying and grinding dyes cotton in greenish-tinged yellow shades.

Further greenish-tinged yellow reactive dyestuffs K—N=N—D—X are obtained by reaction of the following components.

| Ex. | Diazo component $H_2N-D-X$ | X | Coupling compoent KH |
|---|---|---|---|
| 26 | 4-(N-methyl-N-X-aminomethyl)-2-amino-benzenesulfonic acid (SO₃H, NH₂, CH₃—N(X)—CH₂—) | 2-sulfophenyl-NH—C(=N-triazine with isopropylidene and Cl) | 1-(2-sulpho-ethyl)barbituric acid |
| 27 | " | N-phenyl(with CH₂-CH₂-SO₂-CH₂-CH₂-OSO₃H chain)—C(=N-triazine, Cl) | 1-(2-sulpho-ethyl)barbituric acid |
| 28 | " | N-phenyl(with CH₂-CH₂-SO₂-CH₂-CH₂-OSO₃H chain)—C(=N-triazine, F) | 1-(2-sulpho-ethyl)barbituric acid |
| 29 | " | " | 1-carboxy-methylbarbituric acid |
| 30 | " | " | 1,3-bis-(2-hydroxy-ethyl)barbituric acid |
| 31 | " | HO₃S—CH₂—CH₂—NH—C(=N-triazine, Cl) | 1,3-bis-(2-hydroxy-ethyl)barbituric acid |
| 32 | 4-(N-methyl-N-X-aminomethyl)-2-amino-benzenesulfonic acid (SO₃H, NH₂, H₃C—N(X)—CH₂—) | 2-methoxy-5-sulfophenyl-NH—C(=N-triazine, Cl) (OCH₃, SO₃H) | 1-carboxy-methylbarbituric acid |
| 33 | " | HO₃S—CH₂—CH₂—NH—C(=N-triazine, Cl) | 1-carboxy-methylbarbituric acid |
| 34 | " | " | 1-(3-carboxy-propyl)-barbituric acid |

| Ex. | Diazo component $H_2N-D-X$ | X | Coupling compoent KH |
|---|---|---|---|
| 35 | " | ![structure: 2-sulfophenyl-NH-C(=N-triazine with Cl and F)] HO$_3$S-C$_6$H$_4$-NH-C(=N-)-N=C(Cl)-N=C(-) | 1-(3-carboxy-propyl)-barbituric acid |
| 36 | " | " | 1-(2-hydroxyethyl)barbituric acid |
| 37 | 2-amino-4-(N-methyl-N-X-aminomethyl)benzenesulfonic acid (SO$_3$H, NH$_2$, H$_3$C-N(X)-CH$_2$-) | N-(2-sulfatoethylsulfonyl)ethyl-N-phenyl-triazine with F | 1-(2-hydroxyethyl)barbituric acid |
| 38 | 2-amino-4-methoxy-5-(X-aminomethyl)benzenesulfonic acid (SO$_3$H, NH$_2$, H$_3$CO, CH$_2$-NH-X) | morpholino-triazine with F | 1-(2-hydroxyethyl)barbituric acid |
| 39 | " | " | 1-(2-sulphoethyl)barbituric acid |
| 40 | " | HO-CH$_2$CH$_2$-N(phenyl)-triazine with F | 1-(2-sulphoethyl)barbituric acid |
| 41 | " | 3-(sulfatoethylsulfonylmethyl)phenyl-NH-triazine with F (H-N-, SO$_2$-CH$_2$CH$_2$-OSO$_3$H) | 1-(2-sulphoethyl)barbituric acid |

EXAMPLE 42

0.29 mol of 4-(2-sulphatoethyl)sulphonylaniline is diazotized in a known manner and the diazotization product is added to a neutral solution, cooled to 15° C., of 0.29 mol of 4-(4'-amino-2'-sulphophenyl)-amino-5-chloro-2,6-difluoropyridine in 2 l of water. During the coupling reaction, a pH of 5.5 is maintained with sodium carbonate solution. The aqueous coupling solution is cooled to 0°–5° C. 70 ml of 30% strength sodium nitrite solution are added at pH=2.5 to 2.8. The diazotization mixture is subsequently stirred at 0° to 5° C. for 1 hour. Excess nitrite is then destroyed by addition of amidosulphonic acid.

0.32 mol of 1-(2-sulphoethyl)barbituric acid is sprinkled in. A pH of 6.5 is established with sodium carbonate solution. When the coupling reaction has ended, the dyestuff is precipitated by ethanol, filtered off with suction and dried. The dyestuff has the formula

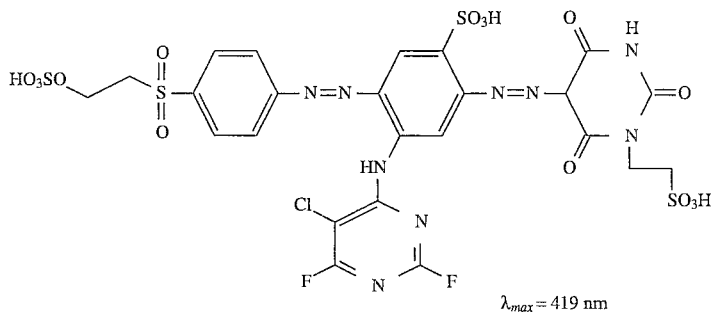

λ_max = 419 nm and dyes cotton in reddish-tinged yellow shades. Further similar reactive dyestuffs K—N=N—D—X which dye cellulose fibres reddish-tinged yellow are obtained if the components shown in the following summary are reacted with one another.

| Ex. | Diazo component H₂N—D—X | X | Coupling component KH |
|---|---|---|---|
| 43 | (structure: HO-S(O)₂-C₆H₄-N=N-C₆H₂(SO₃H)(NH₂)(NHX)) | (Cl, F vinyl-triazine structure) | 1-(2-sulpho-ethyl)barbituric acid λ_max = 420 nm |
| 44 | " | (phenyl-N with SO₂-CH₂CH₂-OSO₃H and fluorotriazine) | 1-(2-sulpho-ethyl)barbituric acid λ_max = 418 nm |
| 45 | " | (2-OCH₃-5-SO₃H-phenyl-NH-chlorotriazine) | 1-(2-sulpho-ethyl)barbituric acid λ_max = 420 nm |
| 46 | " | " | 1-carboxy-methyl-3-(2-hydroxyethyl-)barbituric acid λ_max = 421 nm |
| 47 | " | (2-SO₃H-phenyl-NH-fluorotriazine) | 1-carboxy-methylbarbituric acid λ_max = 419 nm |
| 48 | " | (morpholino-fluorotriazine) | 1-(2-hydroxy-ethyl)barbituric acid λ_max = 419 nm |

-continued

| Ex. | Diazo component H₂N—D—X | X | Coupling component KH |
|---|---|---|---|
| 49 | [structure: 4-sulfophenyl-N=N-benzene with SO₃H, NH₂, HN-X substituents] | [structure: HO₃S-CH₂CH₂-NH-C(=N-triazine with Cl)] | 1-(2-hydroxy-ethyl)barbituric acid λ$_{max}$ = 420 nm |
| 50 | [structure: HO₃SO-CH₂CH₂-SO₂-phenyl-N=N-benzene with SO₃H, NH₂, HN-X] | [structure: chloro-fluoro-pyrimidine] | 1-(2-sulpho-ethyl)barbituric acid λ$_{max}$ = 418 nm |
| 51 | " | [structure: phenyl-N(CH₂CH₂SO₂-OSO₃H)-C(=N-triazine with F)] | 1-(2-sulpho-ethyl)barbituric acid λ$_{max}$ = 419 nm |
| 52 | " | [structure: 2-methoxy-5-sulfo-phenyl-NH-C(=N-triazine with F)] | 1-(2-sulpho-ethyl)barbituric acid λ$_{max}$ = 419 nm |
| 53 | " | " | 1-carboxy-methyl-3-(2-hydroxyethyl)-barbituric acid λ$_{max}$ = 420 nm |
| 54 | " | [structure: 2-sulfo-phenyl-NH-C(=N-triazine with F)] | 1-carboxy-methylbarbituric acid λ$_{max}$ = 421 nm |
| 55 | [structure: HO₃SO-CH₂CH₂-SO₂-phenyl-N=N-benzene with SO₃H, NH₂, HN-X] | [structure: morpholino-C(=N-triazine with F)] | 1-(2-hydroxy-ethyl)barbituric acid λ$_{max}$ = 419 nm |
| 56 | " | [structure: HO₃S-CH₂CH₂-NH-C(=N-triazine with Cl)] | 1-(2-hydroxy-ethyl)barbituric acid λ$_{max}$ = 418 nm |

| Ex. | Diazo component H₂N—D—X | X | Coupling component KH |
|---|---|---|---|
| 57 | HO₃SO—CH₂CH₂—SO₂—C₆H₃(SO₃H)—N=N—C₆H₂(SO₃H)(NH₂)(NHX) | Cl-C=C(CH₃)-N=C(F)-N=C(F) (2,4-difluoro-5-chloropyrimidinyl) | 1-(2-hydroxyethyl)barbituric acid $\lambda_{max}$ = 422 nm |

EXAMPLE 58

0.29 mol of 4-(2-sulphatoethyl)sulphonylaniline is diazotized in a known manner. 0.29 mol of m-toluidine is dissolved in 30 ml of glacial acetic acid. The solution is slowly added dropwise to the diazotization mixture. The mixture is then brought to a pH of about 4.0 with 220 ml of 20% strength sodium acetate solution. The orange dyestuff which has precipitated is filtered off, dried and ground. The dyestuff powder is introduced into 400 ml of 20% strength oleum. The temperature rises to 80° C. The solution is stirred at 80° C. for 2 hours and at 60° C. for 3 hours. After cooling to room temperature, the solution is poured onto ice/potassium chloride brine. The dyestuff is filtered off with suction and stirred into 1 l of water. The mixture is subsequently stirred with 70 ml of 30% strength sodium nitrite solution at 20° C. for 1 hour. The excess nitrite is destroyed with amidosulphonic acid. 0.29 mol of 1-(2-sulphoethyl)barbituric acid is sprinkled in. The pH is brought to 6.5 with sodium carbonate solution. The mixture is subsequently stirred at 20° C. for 1 hour. The dyestuff of the formula

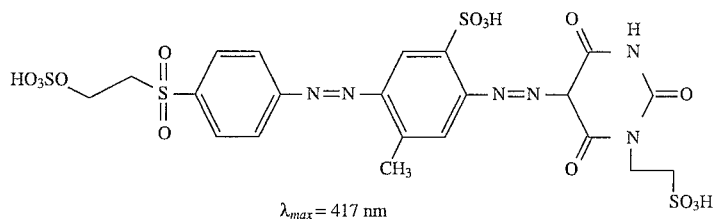

$\lambda_{max}$ = 417 nm obtained after salting out, isolation, drying and grinding dyes cotton in reddish-tinged yellow shades. Further reactive dyestuffs K—N=N—D—SO₂—M which can be prepared analogously are shown below:

| Ex. | Diazo component H₂N-D-SO₂-M | KH |
|---|---|---|
| 59 | HO₃SO—CH₂CH₂—SO₂—C₆H₄—N=N—C₆H₂(SO₃H)(NH₂)(CH₃) | 1-(4-sulphophenyl)barbituric acid $\lambda_{max}$ = 419 nm |
| 60 | " | 1-(2-hydroxyethyl)barbituric acid $\lambda_{max}$ = 417 nm |
| 61 | " | 1-carboxyethyl)barbituric acid |

-continued

| Ex. | Diazo component H$_2$N-D-SO$_2$-M | KH |
|---|---|---|
| | | $\lambda_{max}$ = 419 nm |
| 62 | HO$_3$SO-CH$_2$CH$_2$-SO$_2$-C$_6$H$_4$-N=N-C$_6$H$_3$(SO$_3$H)-NH$_2$ | 1-(2-sulpho-ethyl)barbituric acid $\lambda_{max}$ = 418 nm |
| 63 | " | 1-(5-carboxy-pentyl)barbituric acid $\lambda_{max}$ = 419 nm |
| 64 | " | 1-(2-carboxy-ethyl)barbituric acid $\lambda_{max}$ = 418 nm |
| 65 | HO$_3$SO-CH$_2$CH$_2$-SO$_2$-C$_6$H$_4$-N=N-C$_6$H$_2$(SO$_3$H)(CH$_3$)-NH$_2$ | 1-(2-carboxy-ethyl)barbituric acid $\lambda_{max}$ = 419 nm |
| 66 | HO$_3$SO-CH$_2$CH$_2$-SO$_2$-C$_6$H$_4$-N=N-C$_6$H$_2$(SO$_3$H)(CH$_3$)-NH$_2$ | 1-(2-sulpho-ethyl)barbituric acid $\lambda_{max}$ = 417 nm |

EXAMPLE 67

0.39 mol of 2,4,6-trifluoro-1,3,5-triazine is added to a solution of 0.348 mol of 1-aminobenzenesulphonic acid in 1 l of water at 0° C. and pH=4 to 4.5 in the course of 5 to 10 minutes. The mixture is subsequently stirred for 10 minutes. 120 g of sodium bicarbonate are added to a neutral solution of 0.29 mol of the triazole of the formula

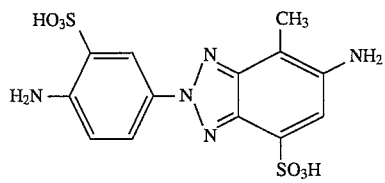

in 2.5 l of water. After the solution has been cooled to 15° C., the above mixture is added in the course of 10 to 15 minutes. The mixture is subsequently stirred at room temperature for 2 to 3 hours. After the mixture has been cooled to 0° to 5° C. and 70 ml of 30% strength sodium nitrite solution have been added, a pH of 2.8 to 3.0 is established with 30% strength hydrochloric acid.

The mixture is subsequently stirred for 30 minutes. After the excess sodium nitrite has been destroyed with amidosulphonic acid, 0.3 mol of 1-(2'-sulphoethyl)barbituric acid is added to the diazotization mixture. A pH of 6.5 is established with sodium carbonate solution. The mixture is subsequently stirred at room temperature and pH=6.5 for one hour. The dyestuff of the formula

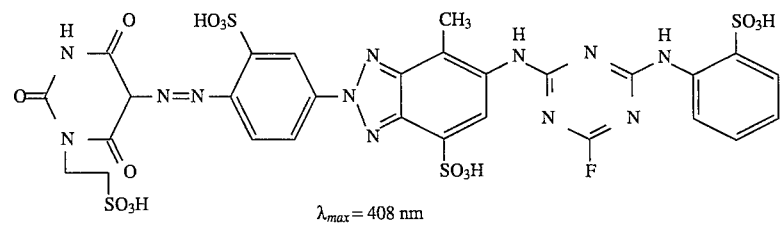

$\lambda_{max}$ = 408 nm obtained after salting out, isolation, drying and grinding dyes cotton in greenish-tinged yellow shades.

EXAMPLE 68

0.334 mol of 2,4,6-trifluoro-1,3,5-triazine is added to a solution of 0.29 mol of triazole of the formula

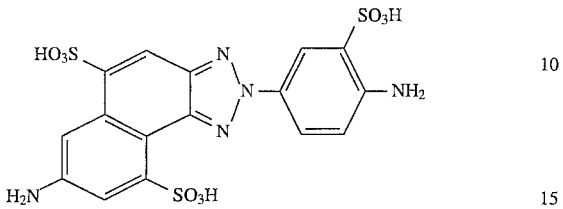

in 3.8 l of water at 0° C. and pH=6.5 in the course of about 10 minutes. A pH of 5.5 is maintained with sodium bicarbonate solution. After 10 minutes, 0.318 mol of N-(2-hydroxyethyl)aniline is added. A pH of 7.6 is established with sodium carbonate solution. The mixture is subsequently stirred at room temperature for 2 hours. Diazotization is then carried out at 5° to 10° C. and pH=2.8. After the excess nitrite has been destroyed, 3 mol of 1-(2-sulphoethyl)barbituric acid are added to the diazotization mixture. A pH of 6.5 to 7 is established with sodium carbonate solution. The dyestuff of the formula

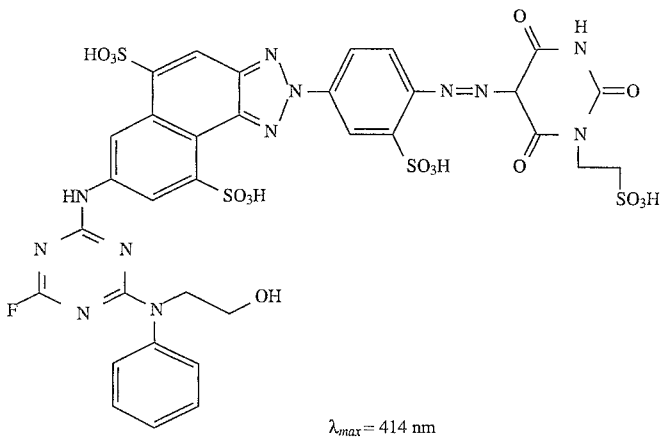

$\lambda_{max} = 414$ nm obtained after salting out, isolation, drying and grinding dyes cotton in greenish-tinged yellow shades.

Further useful reactive dyestuffs of this type K—N=N—D—X can be prepared analogously.

| Ex. | Diazo component $H_2N-D-X$ | X | Coupling component KH |
|---|---|---|---|
| 69 | ![structure] | ![structure] | 1-(2-sulphoethyl)barbituric acid $\lambda_{max} = 415$ nm |

| Ex. | Diazo component H$_2$N—D—X | X | Coupling component KH |
|---|---|---|---|
| 70 | " | [structure: 4-methoxy-2-sulphophenyl-NH-C(=N-triazine with F and CH$_3$)] | 1-(2-sulphoethyl)barbituric acid λ$_{max}$ = 414 nm |
| 71 | " | [structure: phenyl-N(CH$_2$CH$_2$SO$_2$CH$_2$CH$_2$OSO$_3$H)-C(=N-triazine with F and CH$_3$)] | 1-(2-sulphoethyl)barbituric acid λ$_{max}$ = 415 nm |
| 72 | " | " | 1-carboxyethylbarbituric acid λ$_{max}$ = 413 nm |
| 73 | " | " | 1-(4-sulphophenyl)-barbituric acid λ$_{max}$ = 415 nm |
| 74 | " | [structure: 1-SO$_3$H, 5-SO$_3$H naphthyl-NH-C(=N-triazine with F and CH$_3$)] | 1-(2-sulphoethyl)-barbituric acid λ$_{max}$ = 414 nm |
| 75 | " | [structure: 3-sulphophenyl-NH-C(=N-triazine with F and CH$_3$)] | 1-(2-sulphoethyl)-barbituric acid λ$_{max}$ = 414 nm |

EXAMPLE 76

0.32 mol of 2,4,6-trichloro-1,3,5-triazine is suspended in 200 ml of water at 0° C. A neutral solution of 0.3 mol of 3-amino-4-methoxybenzenesulphonic acid in 1 l of water is added to this mixture in the course of 20 minutes. A pH of 4.5 to 5.0 is maintained with sodium carbonate solution. The mixture is subsequently stirred at 0° to 5° C. for 1 hour. Excess 2,4,6-trichloro-1,3,5-triazine is filtered off.

120 g of sodium bicarbonate are added to a neutral solution of 0.29 mol of the triazole of the formula

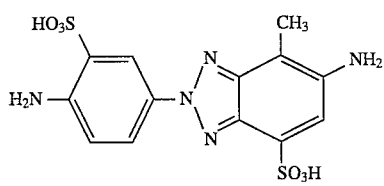

in 2.5 l of water. After the solution has been cooled to 15° C., the above mixture is added in the course of 10 to 15 minutes. The mixture is subsequently stirred at 40° C. for 1 hour. After the mixture has been cooled to 0° to 5° C. and 70 ml of 30% strength sodium nitrite solution have been added, a pH of 2.8 to 3.0 is established with 30% strength hydrochloric acid.

The mixture is subsequently stirred for 30 minutes. After the excess sodium nitrite has been destroyed with amidosulphonic acid, 0.3 mol of 1-(2'-sulphoethyl)-barbituric acid is added to the diazotizationmixture. A pH of 6.5 is established with sodium carbonate solution. The mixture is subsequently stirred at room temperature and pH=6.5 for one hour. The dyestuff of the formula

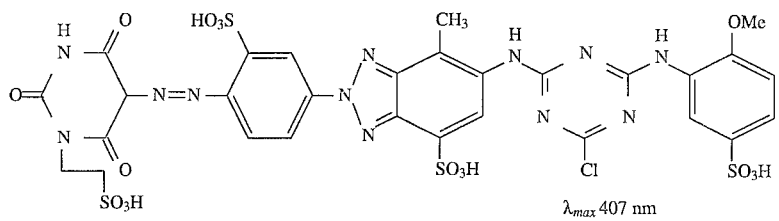

$\lambda_{max}$ 407 nm obtained after salting out, isolation, drying and grinding dyes cotton in greenish-tinged yellow shades.

Further corresponding dyestuffs K—N=N—D—X are:

| Ex. | Diazo component H₂N-D-X | X | Coupling component KH |
|---|---|---|---|
| 77 | 4-methyl-6-(X-NH)-7-SO₃H-2-(4-amino-3-sulfophenyl)benzotriazole | 3-sulfophenyl-NH-C(=N-triazine)-N, triazine with F | 1-(2-sulpho-ethyl)barbituric acid $\lambda_{max}$ = 407 nm |
| 78 | " | 4-methoxy-2-sulfophenyl-NH-C(=N-triazine)-N, triazine with F | 1-(2-sulpho-ethyl)barbituric acid $\lambda_{max}$ = 408 nm |
| 79 | " | 4-(β-sulfatoethylsulfonyl)phenyl-NH-C(=N-triazine)-N, triazine with F | 1-(2-sulpho-ethyl)barbituric acid $\lambda_{max}$ = 407 nm |
| 80 | " | 4-sulfophenyl-NH-C(=N-triazine)-N, triazine with Cl | 1-(2-sulpho-ethyl)barbituric acid $\lambda_{max}$ = 407 nm |
| 81 | " | 2,5-disulfophenyl-NH-C(=N-triazine)-N, triazine with Cl | 1-(2-sulpho-ethyl)barbituric acid $\lambda_{max}$ = 408 nm |
| 82 | " | 1-sulfonaphth-2-yl-NH-C(=N-triazine)-N, triazine with F | 1-(2-sulpho-ethyl)barbituric acid $\lambda_{max}$ = 409 nm |

| Ex. | Diazo component H₂N-D-X | X | Coupling component KH |
|---|---|---|---|
| 83 | (structure: X-NH-, CH₃, SO₃H, benzotriazole with N-phenyl-NH₂-SO₃H) | (structure: HO₃S-naphthalene-SO₂CH₂CH₂OSO₃H with NH-triazine-F) | 1-(2-sulpho-ethyl)barbituric acid $\lambda_{max} = 408$ nm |
| 84 | " | (structure: HO₃S-phenyl-NH-triazine-F) | 1-carboxy-methylbarbituric acid $\lambda_{max} = 409$ nm |
| 85 | " | " | 1-carboxy-methylbarbituric acid $\lambda_{max} = 409$ nm |
| 86 | " | " | 1-(2-hydroxy-ethyl)barbituric acid $\lambda_{max} = 411$ nm |
| 87 | " | " | 1,3-bis-(2-hydroxy-ethyl)barbituric acid $\lambda_{max} = 412$ nm |

EXAMPLE 88

0.334 mol of 2,4,6-trifluoro-1,3,5-triazine is added to a solution of 0.29 mol of the triazole of the formula

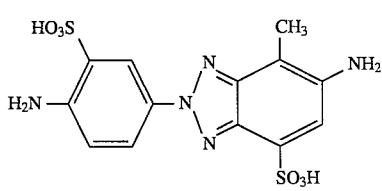

in 3 l of water at 0° C. and pH=4 to 4.5. After 10 minutes, 0.318 mol of 3-aminobenzyl-β-sulphatoethylsulphone is added. A pH of 7 to 7.5 is established and maintained with sodium carbonate solution. The mixture is subsequently stirred at room temperature for 2 hours. Diazotization is then carried out at 0° to 5° C. and pH=2.8 to 3.0. After the excess nitrite has been destroyed, 0.3 mol of 1,3-bis-(2-hydroxypropyl)barbituric acid is added to the diazotization mixture. A pH of 6.5 to 7.0 is established with sodium carbonate solution. The dyestuff of the formula

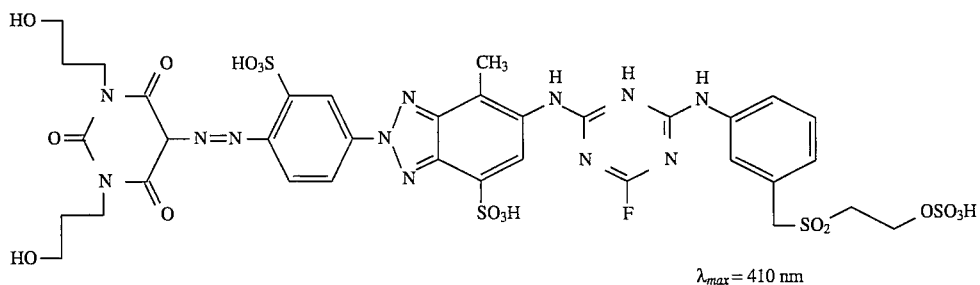

$\lambda_{max} = 410$ nm obtained after salting out, isolation, drying and grinding dyes cotton in greenish-tinged yellow shades.

EXAMPLE 89

0.334 mol of 2,4,6-trifluoro-1,3,5-triazine is added to a solution of 0.29 mol of the triazole of the formula

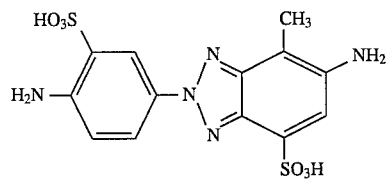

in 3 l of water at 0° C. and pH=4 to 4.5. After 10 minutes, 0.318 mol of morpholine is added. A pH of 7 to 7.5 is established and maintained with sodium carbonate solution. The mixture is subsequently stirred at room temperature for 2 hours. Diazotization is then carried out at 0° to 5° C. and pH=2.8 to 3.0. After the excess nitrite has been destroyed, 0.3 mol of 1-(2-sulphoethyl)barbituric acid is added to the diazotization mixture. A pH of 6.5 to 7.0 is established with sodium carbonate solution. The dyestuff of the formula

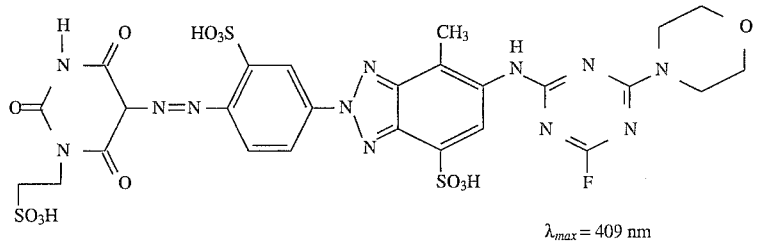

obtained after salting out, isolation, drying and grinding dyes cotton in greenish-tinged yellow shades with a high level of fastness. This usefuldyestuff can also be prepared alternatively as follows:

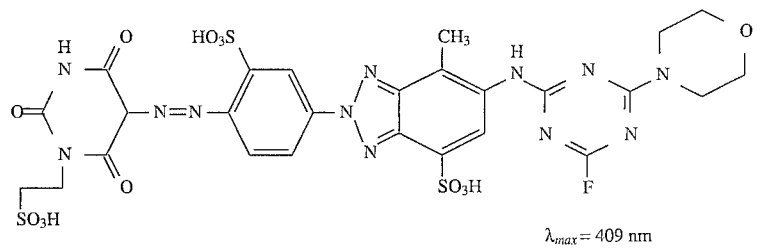

EXAMPLE 90

0.29 mol of the triazole of the formula

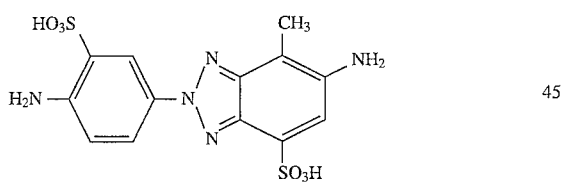

is suspended in 2 l of water of pH=6.0. 0.45 mol of maleic anhydride is introduced in portions into the suspension at 5° C. in the course of 60 minutes, during which the pH is kept at 6.0 with 20% strength sodium hydroxide solution. The mixture is subsequently stirred for 30 minutes. 70 ml of 30% strength sodium nitrite solution are added to the solution. A pH of 2.0 to 2.5 is established with hydrochloric acid. The diazotization mixture is subsequently stirred at 5° to 10° C. for 45 minutes. After the excess nitrite has been destroyed with amidosulphonic acid, 0.3 mol of 1-(2-sulphoethyl)barbituric acid is added to the diazotization mixture. A pH of 6.5 to 7.0 is established with sodium carbonate solution. The mixture is subsequently stirred at room temperature for 15 minutes. It is then heated to 80° C. A pH of 0.5 to 1.0 is established with concentrated hydrochloric acid. After 2 hours, the mixture is allowed to cool. The orange precipitate formed is filtered off with suction and dissolved in 7 l of water at pH=7.0 and 60° C. The solution is then cooled rapidly to 0°C. 0.32 mol of 2,4,6-trifluoro-1,3,5-triazine is added at pH=4 to 4.5. After 10 minutes, 0.3 mol of morpholine is added dropwise.

A pH of 7.0 to 7.5 is established and maintained with sodium carbonate solution. The mixture is subsequently stirred at room temperature for 2 hours. The dyestuff of the formula

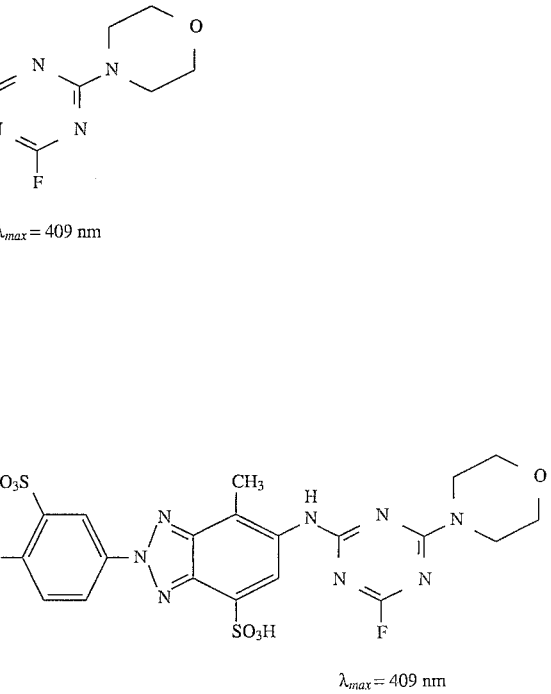

obtained after salting out, isolation, drying and grinding dyes cotton in greenish-tinged yellow shades with a high fastness level.

Further interesting reactive dyestuffs K—N=N—D—X are accessible in accordance with these or the preceding instructions:

| Ex. | Diazo component H₂N-D-X | X | Coupling component KH |
|---|---|---|---|
| 91 | (benzotriazole structure with CH₃, SO₃H, N=N-phenyl-SO₃H/NH₂, X—NH) | phenyl-N(CH₂CH₂OH)-C(=N-triazine-CH₃)(N=C-F) | 1-(2-sulphoethyl)barbituric acid $\lambda_{max}$ = 407 nm |
| 92 | " | HO₃S-CH₂CH₂-NH-C(=N-triazine-CH₃)(N=C-F) | 1-(2-sulphoethyl)barbituric acid $\lambda_{max}$ = 407 nm |
| 93 | " | HO₃S-CH₂CH₂-N(CH₃)-C(=N-triazine-CH₃)(N=C-Cl) | 1-(2-sulphoethyl)barbituric acid $\lambda_{max}$ = 407 nm |
| 94 | " | HO₃S-CH₂-N(CH₃)-C(=N-triazine-CH₃)(N=C-Cl) | 1-(2-sulphoethyl)barbituric acid $\lambda_{max}$ = 407 nm |
| 95 | " | HO₂C-piperidinyl-C(=N-triazine-CH₃)(N=C-F) | 1-(2-sulphoethyl)barbituric acid $\lambda_{max}$ = 407 nm |
| 96 | (benzotriazole structure with CH₃, SO₃H, N=N-phenyl-SO₃H/NH₂, X—NH) | HO₃SO-CH₂CH₂-N(phenyl)-C(=N-triazine-CH₃)(N=C-F) | 1-(2-sulphoethyl)barbituric acid $\lambda_{max}$ = 407 nm |
| 97 | " | Cl-C(=C-CH₃-N)(F)=N-C-F (triazine with Cl, F, F) | 1-(2-sulphoethyl)barbituric acid $\lambda_{max}$ = 408 nm |
| 98 | " | " | 1-carboxyethylbarbituric acid $\lambda_{max}$ = 407 nm |
| 99 | " | morpholinyl-C(=N-triazine-CH₃)(N=C-F) | 1-carboxyethylbarbituric acid $\lambda_{max}$ = 407 nm |

| Ex. | Diazo component H₂N-D-X | X | Coupling component KH |
|---|---|---|---|
| 100 | " | [N-phenyl-N-(2-hydroxyethyl) group attached to triazine with F] | 1-carboxy-ethylbarbituric acid $\lambda_{max} = 407$ nm |
| 101 | " | " | 1-(2-hydroxyethyl)barbituric acid $\lambda_{max} = 409$ nm |
| 102 | " | " | 1-(2-sulphoethyl)barbituric acid $\lambda_{max} = 407$ nm |
| 103 | [benzotriazole structure with CH₃, SO₃H, NH-X, and phenyl-NH₂-SO₃H] | [morpholinoethyl-triazine with F] | 1-(2-hydroxyethyl)barbituric acid $\lambda_{max} = 409$ nm |
| 104 | " | " | 1-(5-carboxy-pentyl)barbituric acid $\lambda_{max} = 409$ nm |
| 105 | " | [N-phenyl-N-(2-hydroxyethyl) triazine with F] | 1-(5-carboxy-pentyl)barbituric acid $\lambda_{max} = 408$ nm |
| 106 | " | [morpholinoethyl-triazine with F] | 1,3-bis-(2-hydroxyethyl)barbituric acid $\lambda_{max} = 411$ nm |
| 107 | " | [pyrimidine with Cl, F] | 1,3-bis-(2-sulphatoethyl)-barbituric acid $\lambda_{max} = 410$ nm |

We claim:

1. Fibre-reactive azo dyestuff of the formula (1) or a tautomer thereof

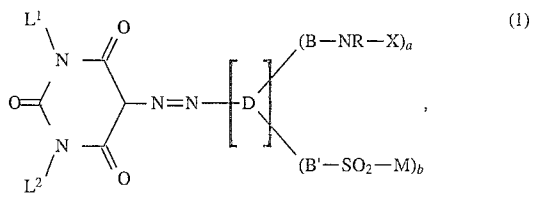

wherein
a=0, 1 or 2,
b=0, 1 or 2,
a+b=1 or 2,
D=the radical of an aromatic or heterocyclic diazo component,
B and B'=independently of one another a direct bond or bridge member,
X=a fibre-reactive heterocyclic radical,
R=H or unsubstituted or substituted $C_1$-$C_4$-alkyl,
M=$CH_2$—$CH_2$—OH, CH=$CH_2$ or $CH_2$—$CH_2$—V, wherein V=a radical which can be eliminated under alkaline conditions, and
$L^1$ and $L^2$=as identical or different radicals, H or an aliphatic or aromatic group, wherein at least one of the substituents $L^1$ and $L^2$ is substituted by at least one polar radical or represents hydroxyl.

2. A dyestuff according to claim 1, wherein

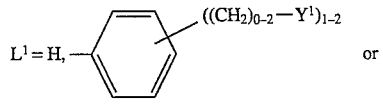

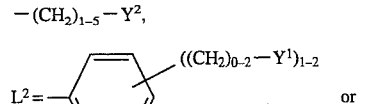

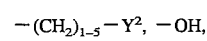

$Y^1$=independently of one another in $L^1$ and $L^2$: OH, COOH, $SO_3H$, $C_1$-$C_4$-alkoxy, hydroxy-$C_{1-4}$-alkoxy, HO—($CH_2$—$CH_2$—O)$_{2-3}$—, HOOC—($CH_2$—$CH_2$—O)$_{1-3}$—, $HO_3S$—($CH_2$—$CH_2$—O)$_{1-3}$, $HO_3S$—$CH_2$—$CH_2$—$CH_2$—O—, or HOOC—$CH_2$—$CH_2$—$CH_2$—O—, and $Y^2$=independently of one another in $L^1$ and $L^2$: OH, COOH, $OSO_3H$, $SO_3H$, $C_1$-$C_4$-alkoxy, hydroxy-$C_{1-4}$-alkoxy, HO—($CH_2$—$CH_2$—O)$_{2-3}$—, HOOC—($CH_2$—$CH_2$—O)$_{1-3}$—, $HO_3S$—($CH_2$—$CH_2$—O)$_{1-3}$, $HO_3S$—$CH_2$—$CH_2$—$CH_2$—O—, HOOC—$CH_2$—$CH_2$—

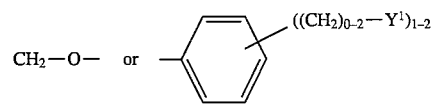

3. A dyestuffs of the formula (1) according to claim 1, wherein
a=0, and —D—(B'—$SO_2$—M)$_b$ corresponds to a radical of the following formula (3)

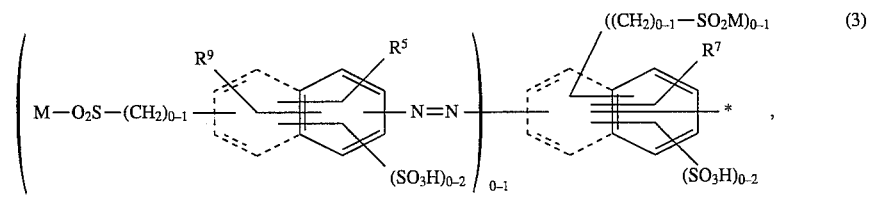

wherein $R^5$ denotes H, $C_1$-$C_4$-alkyl, Cl, Br, $C_1$-$C_4$-alkoxy or COOH, $R^6$ denotes H, $C_1$-$C_4$-alkyl, $C_1$-$C_4$-alkoxy, $SO_3H$, Cl or Br, $R^7$ denotes H, $C_1$-$C_4$-alkyl, $C_1$-$C_4$-alkoxy, Cl, Br, acylamino in particular $C_1$-$C_4$alkylcarbonylamino or arylcarbonylamino, such as unsubstituted or substituted phenylcarbonylamino, $C_1$-$C_4$-alkylsulphonylamino, aminocarbonylamino or arylsulphonylamino, and the bond identified with * is bonded to the azo group of the formula (1).

4. A dyestuff of the formula (1) according to claim 1, wherein
b=0 and
a=1.

5. Dyestuff according to claim 1 of the formula (4)

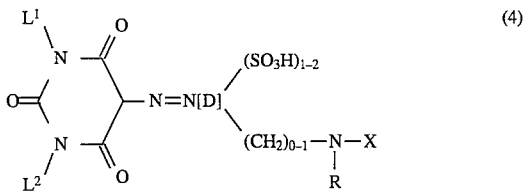

or of the formula (5)

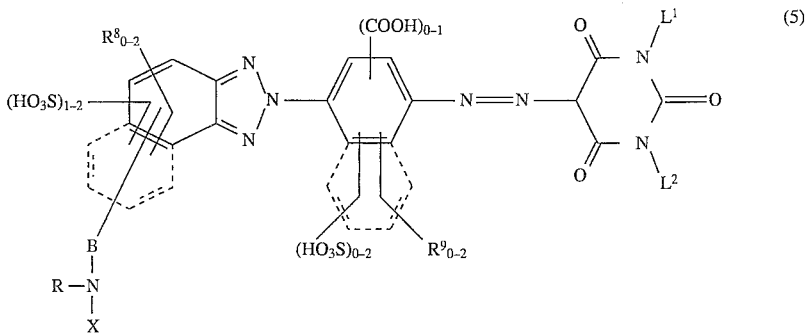

or of the formula (6)

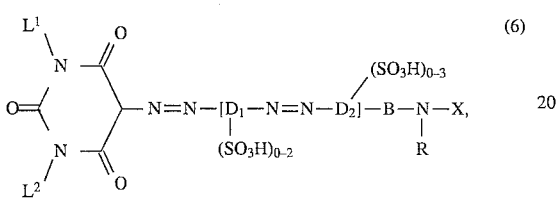

wherein

D = the radical of a benzene or naphthalene, which is unsubstituted or substituted by $C_1$–$C_4$-alkyl, $C_1$–$C_4$-alkoxy, $CO_2H$,

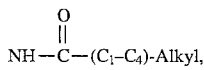

NH—CO—$NH_2$ or halogen, $R^8$ and $R^9$ independently of one another represent hydrogen, $C_1$–$C_4$-alkyl, $C_1$–$C_4$-alkoxy, acetylamino, $NH_2$, methylamino, ethylamino, carbamoyl, ureido, hydroxyl or acetyl, $D_1$ and $D_2$ independently of one another denote a phenylene or naphthylene radical, which is unsubstituted or substituted by $C_1$–$C_4$-alkyl, $C_1$–$C_4$-alkoxy, $CO_2H$, NHCO-$C_1$–$C_4$-alkyl, $NHCONH_2$ or halogen, and $L^1$, $L^2$, R, B and X have the meanings given in claim 1.

6. A dyestuff according to claim 1, which correspond to the formula (7)

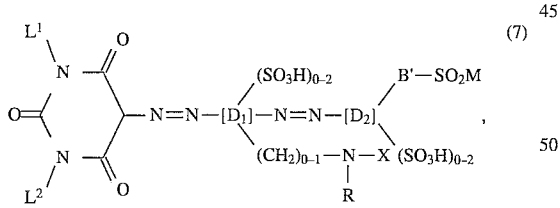

wherein $D_1$ and $D_2$ independently of one another denote a phenylene or naphthylene radical, which is unsubstituted or substituted by $C_1$–$C_4$-alkyl, $C_1$–$C_4$-alkoxy, $CO_2H$,

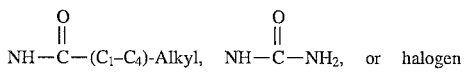

and $L^1$, $L^2$, M, B', R and X have the meanings according to claim 1.

7. A dyestuff according to claim 1, wherein

B and B' independently of one another denote a direct bond or a bridge member of the formulae

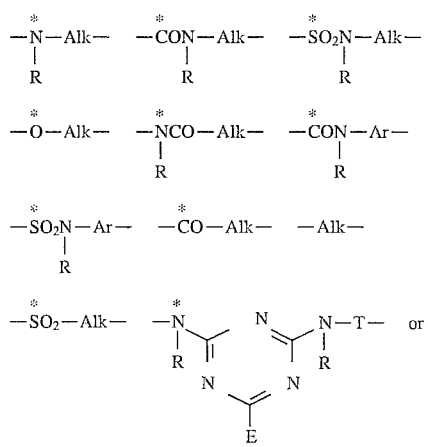

wherein the asterisk marks the linking point with a benzene or naphthalene radical and wherein Alk denotes straight-chain or branched $C_1$–$C_4$-alkylene which is uninterrupted or interrupted by heteroatoms or groupings containing heteroatoms such as N, O or S, Ar denotes unsubstituted or substituted phenylene or naphthylene or the radical of a diphenyl or stilbene, T denotes Alk or Ar or —Ålk—Ar— wherein Alk or Ar are unsubstituted or substituted by F, Cl, Br, $C_1$–$C_4$-alkyl, $C_1$–$C_4$-alkoxy, carboxyl or sulpho, and E denotes F, Cl, Br, unsubstituted or substituted amino, OH, $C_1$–$C_4$-alkoxy, unsubstituted or substituted phenoxy or $C_1$–$C_4$-alkylthio, and X represents

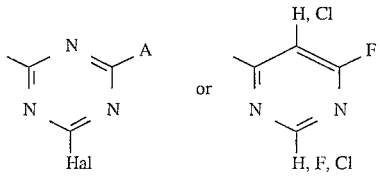

wherein

Hal = Cl or F and

A = the radical of an amine AH.

8. A material which contains cellulose or polyamide which is dyed with a reactive dyestuff according to claim 1.

9. A compound of the formula

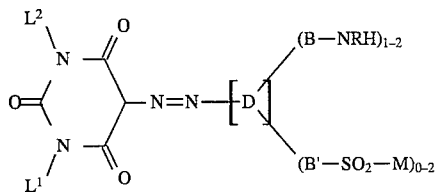

wherein $L^1$ and $L^2$ = as identical or different radicals, H or an aliphatic or aromatic group, wherein at least one of the substituents $L^1$ and $L^2$ is substituted by at least one polar radical or represents hydroxyl.

B and B' = independently of one another a direct bond or bridge member,

R = H or unsubstituted or substituted $C_1$–$C_4$-alkyl,

D = the radical of an aromatic or heterocyclic diazo component,

M = $CH_2$—$CH_2$—OH, CH=$CH_2$ or $CH_2$—$CH_2$—V, wherein V = a radical which can be eliminated under alkaline conditions.

* * * * *

UNITED STATES PATENT AND TRADEMARK OFFICE
CERTIFICATE OF CORRECTION

PATENT NO. : 5,502,174
DATED : March 26, 1996
INVENTOR(S) : Ehrenberg, et al.

It is certified that error appears in the above-indentified patent and that said Letters Patent is hereby corrected as shown below:

Col. 58, line 21    Delete " Dyestuff " and substitute -- A dyestuff --

Col. 60, line 39    Delete " $C_1$-$C_4$-alkylene " and substitute -- $C_1$-$C_6$-alkylene --

Signed and Sealed this

Twenty-seventh Day of August, 1996

Attest:

BRUCE LEHMAN

Attesting Officer

Commissioner of Patents and Trademarks